US008232075B2

(12) United States Patent
Luan et al.

(10) Patent No.: US 8,232,075 B2
(45) Date of Patent: Jul. 31, 2012

(54) RATIONALLY DESIGNED MEDIA FOR CELL CULTURE

(75) Inventors: Yen-Tung Luan, Chelmsford, MA (US); Wenge Wang, North Chelmsford, MA (US); Ryan Nolan, Stoneham, MA (US); Denis Drapeau, Salem, NH (US)

(73) Assignee: Wyeth LLC, Madison, NJ (US)

( * ) Notice: Subject to any disclaimer, the term of this patent is extended or adjusted under 35 U.S.C. 154(b) by 1029 days.

(21) Appl. No.: 11/936,866

(22) Filed: Nov. 8, 2007

(65) Prior Publication Data

US 2008/0108553 A1 May 8, 2008

Related U.S. Application Data

(60) Provisional application No. 60/858,289, filed on Nov. 8, 2006.

(51) Int. Cl.
*C12P 21/00* (2006.01)
*C12N 5/00* (2006.01)
*A61K 38/02* (2006.01)

(52) U.S. Cl. ......... 435/69.1; 435/325; 435/404; 435/29; 514/2; 530/300

(58) Field of Classification Search ...... 514/2; 530/300; 435/69.1, 325, 404, 29
See application file for complete search history.

(56) References Cited

U.S. PATENT DOCUMENTS

| 4,510,245 | A | 4/1985 | Cousens et al. | 435/69.3 |
| 4,968,615 | A | 11/1990 | Koszinowski et al. | 435/91.41 |
| 5,122,469 | A | 6/1992 | Mather et al. | 435/240.2 |
| 5,168,062 | A | 12/1992 | Stinski | 435/366 |
| 5,399,677 | A | 3/1995 | Wolfman et al. | 536/23.5 |
| 7,294,484 | B2 | 11/2007 | Drapeau et al. | 435/69.1 |
| 7,300,773 | B2 * | 11/2007 | Drapeau et al. | 435/69.1 |
| 7,335,491 | B2 * | 2/2008 | Drapeau et al. | 435/69.1 |
| 8,067,182 | B2 | 11/2011 | Kelley et al. | |
| 2005/0070013 | A1 | 3/2005 | Luan et al. | 435/404 |
| 2006/0121568 | A1 | 6/2006 | Drapeau et al. | |
| 2007/0054390 | A1 | 3/2007 | Kelley et al. | 435/183 |
| 2007/0060741 | A1 | 3/2007 | Kelley et al. | |

FOREIGN PATENT DOCUMENTS

EP 0433225 6/1991

OTHER PUBLICATIONS

Bird et al. (1988), Single-chain Antigen-Binding Proteins, *Science*, vol. 242:423-26.
Bonarius (1996), Metabolic Flux Analysis of Hybridoma Cells in Different Culture Media Using Mass Balances, *Biotechnol. Bioeng.*, vol. 50:299-318.
Castro et al. (1992), Application of a statistical design to the optimization of culture medium for recombinant interferon-gamma production by Chinese hamster ovary cells, *Appl. Microbiol. Biotechnol*, vol. 38:84-90.
Derouazi et al. (2004), Serum-Free Large-Scale Transient Transfection of CHO Cells, *Biotechnol. Bioeng.*, vol. 87(4):537-45.
Durocher et al. (2002), High-Level and high-throughput recombinant protein production by transient transfection of suspension-growing 293-EBNA1 cells, *Nuc. Acids Res.* vol. 30:No. 2 1-9.
Ham (1965), Clonal Growth of Mammalian Cells in a Chemically Defined, Synthetic Medium, *Proc. Nat. Acad. Sci. U.S.A.* vol. 53:288-93.
Huston et al. (1988), Protein engineering of antibody binding sites: Recovery of specific activity in an anti-digoxin single-chain Fv analogue produced in *Escherichia Coli*, *Proc. Natl. Acad. Sci. U.S.A.* 85:5879-83.
Jordan et al. (1998), Calcium-phosphate mediated DNA transfer into HEK-293 cells in suspension: control of physicochemical parameters allows transfection in stirred media, *Cytotechnology* 26(1):39-47.
Kaufman et al. (1991), Improved vectors for stable expression of foreign genes in mamalian cells by use of the untranslated leader sequence from EMC virus, *Nuc. Acids Res.* vol. 19:4485-90.
Kaufman (1990), Selection and Coamplification of Heterologous Genes in Mammalian Cells, Meth. Enzymol. vol. 185:537-66.
Kohno et al. (1990), Refolding of Recombinant Proteins, *Meth. Enzymol.* vol. 185:187-95.
Kostelny et al. (1992), Formation of a Bispecific Antibody by the Use of Leucine Zippers, *J. Immunol.* vol. 148:1547-53.
Kunaparaju et al. (2005), Epi-CHO, an Episomal Expression System for Recombinant Protein Production in CHO cells, *Biotechnol. Bioeng.* vol. 91:670-77.
Lan Pham et al. (2003), Large-Scale Transient Transfection of Serum-Free Suspension-Growing HEK293 EBNA1 Cells: Peptone Additives Improve Cell Growth and Transfection Efficiency, *Biotechnol Bioeng.* 84:332-42.
Lindell et al. (2004), Calfection: a novel gene transfer method for suspension cells, *Biochim. Biophys. Acta* 1676(2):155-61.
Ma ( 2007), Development of a Robust, Chemically-Defined and High-Yielding GS-CHO Platform Production Process, *The Waterside Conference* p. 1-17.
Maiorella et al. (1988), Large-Scale Insect Cell-Culture for Recombinant Protein Production *Bio/Technology* vol. 6:1406-10.
Meissner et al (2001), Transient Gene Expression: Recombinant Protein Production with Suspension-Adapted HEK293-EBNA Cells, Biotechnol. Bioeng. 75:198-203.
Moore et al. (1967), Culture of Normal Human Leukocytes, *J. Am. Medical Assn.* vol. 199:51924.

(Continued)

*Primary Examiner* — Chih-Min Kam
(74) *Attorney, Agent, or Firm* — Pfizer Inc.

(57) ABSTRACT

This invention relates to methods for rationally designing cell culture media for use in cell cultures, e.g., cell cultures employed in polypeptide production; cell culture media designed with the disclosed methods; methods of producing a polypeptide of interest, e.g., an antibody, using such media; polypeptides produced using the methods and media disclosed herein; and pharmaceuticals compositions containing such polypeptides. The rationally designed media contain a concentration of an amino acid that is calculated for use in cell mass, a concentration of the amino acid that is calculated for use in cell maintenance, and a concentration of the amino acid that is calculated for incorporation into the polypeptide of interest.

15 Claims, 15 Drawing Sheets

OTHER PUBLICATIONS

Morton (1970), A survey of commercially available tissue culture media, *In Vitro* vol. 6:89-108.

Nadeau et al. (2000), Human 293 Cell Metabolism in Low Glutamine-supplied Culture: Interpretation of Metabolic changes through Metabolic Flux Analysis, *Metab. Eng.* 2:277-92.

Nyberg et al. (1999), Metabolism of Peptide Amino Acids by Chinese Hamster Ovary Cells Grown in a Complex Medium, *Biotechnol. Bioeng.* 62:324-35.

Rols et al. (1992), Highly efficient transfection of mammalian cells by electric field pulses, *Eur. J. Biochem.* 206(1):115-21.

Sandadi et al. (2005), Heuristic Optimization of Antibody Production by Chinese Hamster Ovary Cells, *Biotechnol. Prog.* 21:1537-1542.

Schlaeger and Christensen (1999), Transient gene expression in mammalian cells grown in serum-free suspension culture, *Cytotechnology* 30(1-3):71-83.

Songsivilai and Lachmann (1990), Bispecific antibody: a tool for diagnosis and treatment of disease, *Clin. Exp. Immunol.* 79:315-21.

Wurm and Bernard (1999), Large-scale transient expression in mammalian cells for recombinant protein production, *Curr. Opin. Biotechnol.* 10(2):156-59.

\* cited by examiner

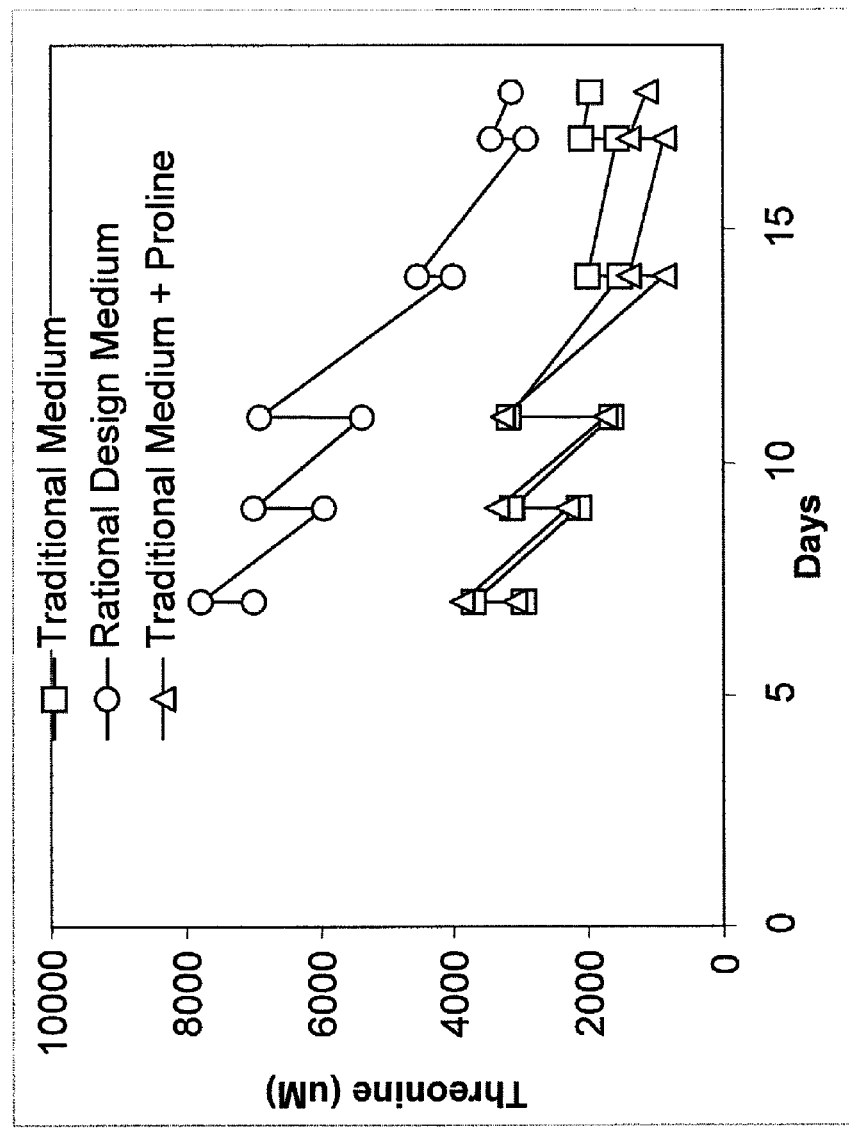

RATIONALLY DESIGNED MEDIA FOR CELL CULTURE

RELATED APPLICATIONS

This application claims the benefit of priority from U.S. Provisional Patent Application No. 60/858,289, filed Nov. 8, 2006, the content of which is hereby incorporated by reference herein in its entirety

BACKGROUND OF THE INVENTION

1. Field of the Invention

This invention relates to methods for rationally designing cell culture media for use in cell cultures employed in, e.g., polypeptide production; cell culture media designed with the disclosed methods; methods of producing large quantities of a polypeptide of interest, e.g., an antibody, using such media; polypeptides produced using the methods and media disclosed herein; and pharmaceuticals compositions containing such polypeptides. The invention is particularly useful in large-scale cell cultures. The methods and compositions disclosed herein are particularly useful to produce significant quantities of polypeptides in batch, fed-batch and perfusion animal cell cultures.

2. Related Background Art

A large proportion of biotechnology products, whether commercially available or only in development, are protein therapeutics; thus, there is a demand for production of these polypeptides in cell cultures. Furthermore, the cellular machinery of an animal cell (as opposed to, e.g., a bacterial cell) is often required to produce many forms of polypeptide therapeutics (such as glycosylated proteins or hybridoma-produced monoclonal antibodies (MAbs)). Consequently, there is an increasing demand for optimizing production of these polypeptides in cell cultures, and particularly in animal cell cultures.

As compared to bacterial cell cultures, animal cell cultures have lower production rates and typically generate lower production yields. Thus, a significant quantity of research focuses on animal cell culture conditions that optimize the polypeptide output, i.e., conditions that support high cell density and high titer. For example, it has been determined that maintaining glucose concentrations in cell culture media at low concentrations and culturing cells in a production phase at an osmolality of about 400 to 600 mOsm increases production of recombinant proteins by animal cell cultures, wherein culturing in all phases is also at a selected glutamine concentration (preferably between about 0.2 to about 2 mM). It has also been determined that restricted feeding of glucose to animal cell cultures in fed-batch processes controls lactate production without requiring the constant-rate feeding of glucose. Further, it is known that modification of the total cumulative concentration of amino acids, the concentration of individual amino acids, and the ratios of individual amino acids to each other (e.g., glutamine to asparagine) and to total amino acids (e.g., glutamine to total amino acids) in the media of a large-scale cell culture can result in substantially improved large-scale polypeptide production.

Traditionally, medium studies for animal cell cultures focus on three techniques: 1) enriching the medium components of the starting medium and increasing the frequency of culture feeding; 2) applying multi-factorial design to different medium strengths and different component concentrations; and 3) analyzing conditioned (spent) medium for amino acids, vitamins, and other components, and adding those components that are at low levels or are depleted. These methods generally use cell density, viability and titer responses as indicators of optimization.

However, the above methods only indirectly detect the nutrient requirement for cells based on the end result, i.e., cell density, viability, and titer, rather than detecting and providing the cell with the actual nutrient requirement for optimized protein production.

SUMMARY OF THE INVENTION

The present invention provides methods for rationally designing cell culture media, e.g., large-scale cell culture media, for use in, e.g. large-scale cell cultures employed in polypeptide production; cell culture media, e.g., large-scale cell culture media, designed with the disclosed methods; methods of producing large quantities of a polypeptide of interest, e.g., an antibody, using such media; polypeptides produced using the methods and media disclosed herein; and pharmaceuticals compositions containing such polypeptides. These methods and compositions are useful for culturing, e.g., batch, fed-batch, and perfusion culturing, of cells. These methods and compositions are particularly useful for large-scale culturing, e.g., batch, fed-batch, and perfusion culturing, of animal cells, e.g., mammalian cells.

A rationally designed medium of the present invention contains a concentration of an amino acid that is calculated for use in cell mass, a concentration of the amino acid that is calculated for use in cell maintenance, and a concentration of the amino acid that is calculated for incorporation into the polypeptide of interest.

In one embodiment, the invention provides a method of producing a polypeptide in a cell culture comprising providing a cell culture, comprising cells, comprising a nucleic acid encoding a polypeptide of interest, and a desired cell culture medium, comprising a concentration of an amino acid that is calculated for use in cell mass, a concentration of the amino acid that is calculated for use in cell maintenance, and a concentration of the amino acid that is calculated for incorporation into the polypeptide of interest; and, maintaining the cell culture under conditions that allow expression of the polypeptide of interest. In one embodiment of the invention, the desired cell culture medium comprises a baseline-adjusted amino acid concentration, A, according to the formula $A=[(M*X)+(N*P)+(Y*M*X)]*F$, wherein X is a concentration of the amino acid that is used per unit of cell mass, P is a concentration of the amino acid that is used for incorporation into the polypeptide of interest per unit of polypeptide titer, M is a multiplier for a desired peak cell density of the cell culture, N is a multiplier for a desired concentration of the polypeptide of interest, Y is a cell maintenance factor, and F is a baseline factor.

In another embodiment, the invention provides a method of producing a polypeptide in a cell culture, comprising providing a cell culture, comprising cells, comprising a nucleic acid encoding a polypeptide of interest; and a starting cell culture medium, wherein the volume of the starting cell culture medium is about 60-99% of the volume of a desired cell culture medium volume; providing a feeding cell culture medium to the cell culture, wherein the volume of the feeding cell culture medium is about 1-40% of the desired cell culture medium volume, and wherein the resulting desired cell culture medium comprises a concentration of an amino acid that is calculated for use in cell mass, a concentration of the amino acid that is calculated for use in cell maintenance, and a concentration of the amino acid that is calculated for incorporation into the polypeptide of interest; and, maintaining the cell culture under conditions that allow expression of the polypeptide of interest. In one embodiment of the invention, the resulting desired cell culture medium comprises a baseline-adjusted amino acid concentration, A, according to the formula $A=[(M*X)+(N*P)+(Y*M*X)]*F$, wherein X is a concentration of the amino acid that is used per unit of cell mass, P is a concentration of the amino acid that is used for incorporation into the polypeptide of interest per unit of polypeptide titer, M is a multiplier for a desired peak cell density of the cell culture, N is a multiplier for a desired concentration of the polypeptide of interest, Y is a cell maintenance factor, and F is a baseline factor; and maintaining the cell culture under conditions that allow expression of the polypeptide of interest. In another embodiment of the invention, the starting cell culture medium comprises a concentration, B, of the amino acid according to the formula $B=[A-(Z*V)]/(1-V)$, wherein Z is a concentration of the amino acid in the feeding cell culture medium, and V is a volume of the feeding culture medium as a proportion of the desired cell culture medium volume. In another embodiment of the methods disclosed herein, Y is 0 to about 1.5. In yet another embodiment of the methods disclosed herein, F is about 1 to about 1.5. In a further embodiment of the methods disclosed herein, Y is 0 to about 1.5 and F is about 1 to about 1.5.

In one embodiment of the methods disclosed herein, the desired cell culture medium comprises greater than or equal to about 3 mM tyrosine. In another embodiments of the methods disclosed herein, the desired cell culture medium comprises: between about 7 mM and about 30 mM leucine; between about 7 mM and about 30 mM lysine; between about 7 mM and about 30 mM threonine; between about 7 mM and about 30 mM proline; and/or between about 7 mM and about 30 mM valine. In a further embodiment of the methods disclosed herein, the combined concentration of leucine, lysine, threonine, proline, and valine in the desired cell culture medium is between about 35 mM and about 150 mM. In yet another embodiment, the combined concentration of leucine, lysine, threonine, and valine in the desired cell culture medium is between about 60% and about 80% of the concentration of the total essential amino acids in the desired cell culture medium.

In one embodiment of the methods disclosed herein, the combined concentration of the essential amino acids in the desired cell culture medium is between about 30% and about 50% of the concentration of the total amino acids in the desired cell culture medium. In another embodiment of the methods disclosed herein, the concentration of amino acids in the desired cell culture medium is between about 120 mM and about 350 mM. In a further embodiment of the methods disclosed herein, the concentration of proline in the cell culture is maintained at greater than about 1 mM. In yet another embodiment of the methods disclosed herein, the concentration of proline in the cell culture is maintained at greater than about 2 mM. In some embodiments of the methods of producing a polypeptide, the cell culture is a large-scale cell culture. In other embodiments, the cells are animal cells.

A further aspect of the invention provides polypeptides produced according to the methods disclosed herein. Another aspect of the invention provides a pharmaceutical composition comprising a polypeptide produced according to the methods disclosed herein and a pharmaceutically acceptable carrier.

A further aspect of the invention provides a method of cell culture comprising: providing a cell culture, comprising: cells; and a desired cell culture medium, comprising a concentration of an amino acid that is calculated for use in cell mass and a concentration of the amino acid that is calculated for use in cell maintenance; and maintaining the cell culture under conditions that allow growth and replication of the cells in the cell culture. In one embodiment of the invention, the desired cell culture medium comprises a baseline-adjusted amino acid concentration, A', according to the formula $A'=[(M*X)+(Y*M*X)]*F$, wherein X is a concentration of the amino acid that is used per unit of cell mass, M is a multiplier for a desired peak cell density of the cell culture, Y is a cell maintenance factor, and F is a baseline factor. In some embodiments of the methods of cell culture, the cell culture is a large-scale cell culture. In other embodiments, the cells are animal cells.

A further aspect of the invention provides a cell culture medium, comprising a total concentration of amino acids from between about 120 mM and about 350 mM. Another aspect of the invention provides a cell culture medium for use in the production of a polypeptide of interest, comprising a total concentration of amino acids from between about 120 mM and about 350 mM.

Another aspect of the invention provides a cell culture medium for use in the production of a polypeptide of interest, comprising a concentration of an amino acid that is calculated for use in cell mass, a concentration of the amino acid that is calculated for use in cell maintenance, and a concentration of the amino acid that is calculated for incorporation into the polypeptide of interest. In one embodiment of the invention, the cell culture medium for use in the production of a polypeptide of interest comprises a baseline-adjusted amino acid concentration, A, according to the formula $A=[(M*X)+(N*P)+(Y*M*X)]*F$, wherein X is a concentration of the amino acid that is used per unit of cell mass, P is a concentration of the amino acid that is used for incorporation into the polypeptide of interest per unit of polypeptide titer, M is a multiplier for desired peak cell density of the cell culture, N is a multiplier for desired concentration of the polypeptide of interest, Y is a cell maintenance factor, and F is a baseline factor.

Yet another aspect of the invention provides a cell culture medium, comprising a baseline-adjusted amino acid concentration, A', according to the formula $A'=[(M*X)+(Y*M*X)]*F$, wherein X is a concentration of the amino acid that is used per unit of cell mass, M is a multiplier for desired peak cell density of the cell culture, Y is a cell maintenance factor, and F is a baseline factor. In some embodiments, the cell culture medium is a large-scale cell culture medium. In other embodiments, the cell culture medium is an animal cell culture medium.

Yet another aspect of the invention provides a method for determining an optimized concentration of an amino acid used in a cell culture medium for the production of a polypeptide of interest in a cell culture, comprising: determining the amino acid concentration required for the cell mass of the cells in the cell culture at a target cell density; determining the amino acid concentration required to produce the polypeptide of interest in the cell culture at a target polypeptide titer; determining the amino acid concentration required for cell maintenance of the cells in the cell culture; and adding the concentrations to provide an optimized concentration of the amino acid used in the cell culture medium for the production of the polypeptide of interest in the cell culture.

A further aspect of the invention provides a method for determining an optimized amino acid concentration, A, of an amino acid used in a cell culture medium for the production of a polypeptide of interest in a cell culture, comprising: determining the amino acid concentration, X, required for cell mass of the cells at a set cell density; determining the amino acid concentration, P, required to produce the polypeptide of interest at a set polypeptide titer; and determining the optimized amino acid concentration, A, according to the formula A=[(M*X)+(N*P)+(M*Y*X)]*F, wherein M is a multiplier for a desired target cell density of the cell culture, N is a multiplier for a desired target concentration of the polypeptide of interest, Y is a cell maintenance factor; and F is a baseline factor. In some embodiments of the methods for determining an optimized amino acid concentration, the cell culture is a large-scale cell culture. In other embodiments, the cells are animal cells.

Other features and advantages of the invention will be apparent from the following detailed description and claims.

DETAILED DESCRIPTION OF THE INVENTION

Figure 1:
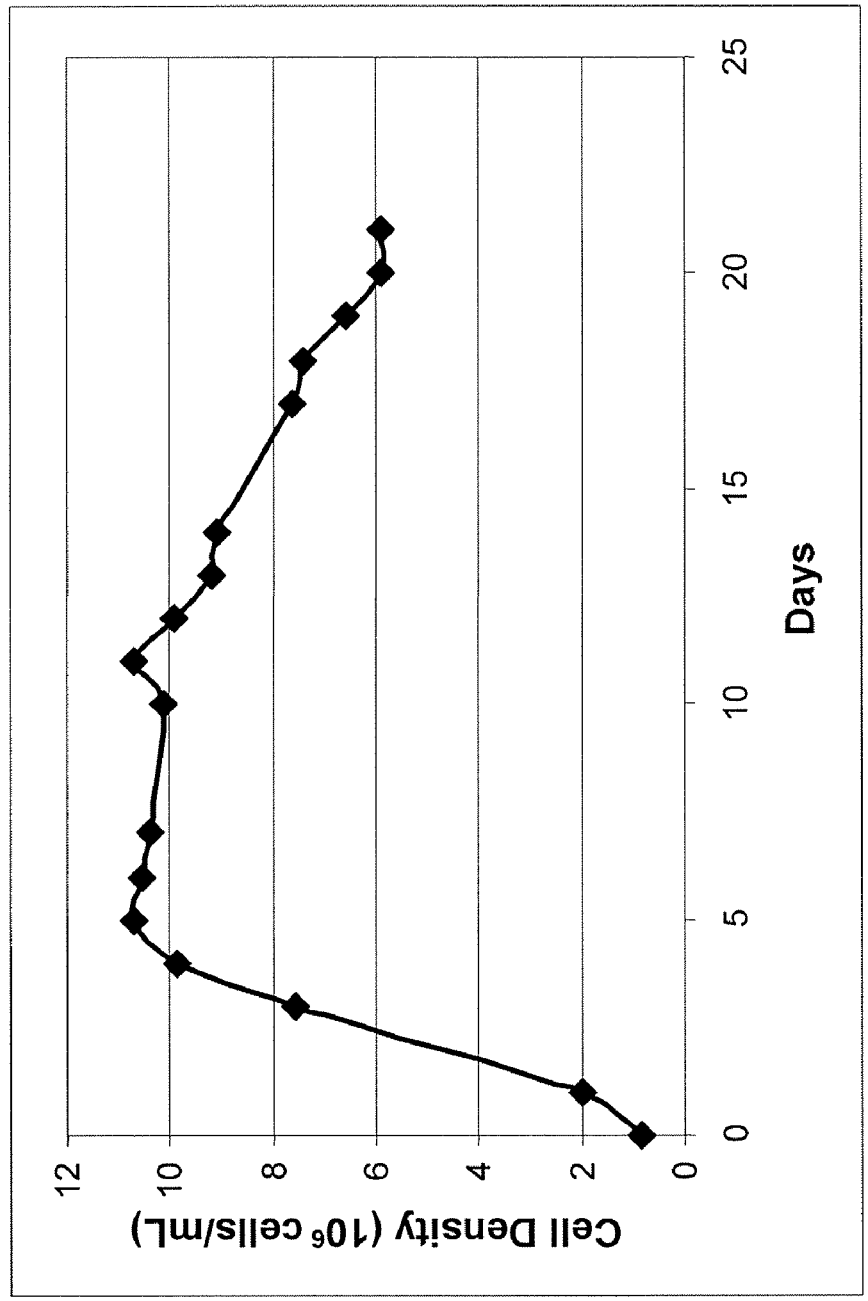
FIG. 1 depicts the cell density (Y-axis; "Cell Density ($10^6$ cells/mL)") over time (X-axis; "Days") for CHO cells engineered to express anti-IL-22. Cells were cultured in the rationally designed medium of Example 2.

The term "batch culture" as used herein refers to a method of culturing cells in which all the components that will ultimately be used in culturing the cells, including the medium as well as the cells themselves, are provided at the beginning of the culturing process. A batch culture is typically stopped at some point and the cells and/or components in the medium are harvested and optionally purified.

The term "fed-batch culture" as used herein refers to a method of culturing cells in which additional components are provided to the culture at some time subsequent to the beginning of the culture process. The provided components typically comprise nutritional supplements for the cells that have been depleted during the culturing process. A fed-batch culture is typically stopped at some point and the cells and/or components in the medium are harvested and optionally purified. In a preferred embodiment of the present invention, the cell culture is an animal cell culture, e.g., a mammalian cell culture, that is a batch or fed-batch culture.

The term "perfusion culture" as used herein refers to a method of culturing cells in which additional components are provided continuously or semi-continuously to the culture subsequent to the beginning of the culture process. The provided components typically comprise nutritional supplements for the cells that have been depleted during the culturing process. Portions of the cells and/or components in the medium are typically harvested on a continuous or semi-continuous basis and are optionally purified.

The term "bioreactor" as used herein refers to any vessel used for the growth of a prokaryotic or eukaryotic cell culture, e.g., an animal cell culture (such as a mammalian cell culture). The bioreactor can be of any size so long as it is useful for the culturing of cells, e.g., mammalian cells. Typically, the bioreactor will be at least 30 ml and may be 1, 10, 100, 250, 500, 1000, 2500, 5000, 8000, 10,000, 12,0000 liters or more, or any intermediate volume. The internal conditions of the bioreactor, including, but not limited to pH and temperature, are typically controlled during the culturing period. The bioreactor can be composed of any material that is suitable for holding mammalian cell cultures suspended in media under the culture conditions of the present invention, including glass, plastic or metal. The term "production bioreactor" as used herein refers to the final bioreactor used in the production of the polypeptide or protein of interest. The volume of a large-scale cell culture production bioreactor is generally greater than about 100 ml, typically at least about 10 liters, and may be 500, 1000, 2500, 5000, 8000, 10,000, 12,0000 liters or more, or any intermediate volume. One of ordinary skill in the art will be aware of, and will be able to choose, suitable bioreactors for use in practicing the present invention.

The terms "cell density," "cell concentration," or the like, as used herein, refer to that number, weight, mass, etc. of cells present in a given volume of medium. "Peak cell density" or the like refers to the maximum number of cells that can be reached in a given volume of medium, and "desired peak cell density" or the like refers to the maximum number of cells that a practitioner desires to obtain (e.g., targets) in a given cell volume. Variations of such target value(s) will be clear to those of skill in the art, e.g., one of skill may express a target value(s) in terms of desired cell mass, and such target value(s) may be in one or more appropriate units of measure (e.g., desired peak units of cell mass).

The term "cell viability" as used herein refers to the ability of cells in culture to survive under a given set of culture conditions or experimental variations. The term as used herein also refers to that portion of cells that are alive at a particular time in relation to the total number of cells, living and dead, in the culture at that time.

The terms "culture" and "cell culture" as used herein refer to a cell population that is suspended in a cell culture medium under conditions suitable to survival and/or growth of the cell population. As used herein, these terms may refer to the combination comprising the cell population (e.g., the animal cell culture) and the medium in which the population is suspended.

The term "integrated viable cell density" or "IVC" as used herein refers to the average density of viable cells over the course of the culture multiplied by the amount of time the culture has run. Assuming the amount of polypeptide and/or protein produced is proportional to the number of viable cells present over the course of the culture, integrated viable cell density is a useful tool for estimating the amount of polypeptide and/or protein produced over the course of the culture.

The terms "medium," "cell culture medium," and "culture medium" as used herein refer to a solution containing nutrients that nourish growing animal, e.g., mammalian, cells. Typically, these solutions provide essential and nonessential amino acids, vitamins, energy sources, lipids, and trace elements required by the cell for minimal growth and/or survival. The solution may also contain components that enhance growth and/or survival above the minimal rate, including hormones and growth factors. The solution is preferably formulated to a pH and salt concentration optimal for cell survival and proliferation. In one embodiment, the medium is a defined medium. Defined media are media in which all components have a known chemical structure. In another embodiment of the invention, the medium may contain an amino acid(s) derived from any source or method known in the art, including, but not limited to, an amino acid(s) derived either from single amino acid addition(s) or from peptone or protein hydrolysate (including animal or plant source(s)) addition(s).

The term "seeding" as used herein refers to the process of providing a cell culture to a bioreactor or another vessel. The cells may have been propagated previously in another bioreactor or vessel. Alternatively, the cells may have been frozen and thawed prior to, e.g., immediately prior to, providing them to the bioreactor or vessel. The term refers to any number of cells, including a single cell.

The term "titer" as used herein refers to the total amount of polypeptide of interest produced by an animal cell culture, divided by a given amount of medium volume; thus "titer" refers to a concentration. Titer is typically expressed in units of milligrams of polypeptide per milliliter of medium.

As used herein, the term "antibody" includes a protein comprising at least one, and typically two, VH domains or portions thereof, and/or at least one, and typically two, VL domains or portions thereof. In certain embodiments, the antibody is a tetramer of two heavy immunoglobulin chains and two light immunoglobulin chains, wherein the heavy and light immunoglobulin chains are interconnected by, e.g., disulfide bonds. The antibodies, or a portion thereof, can be obtained from any origin, including, but not limited to, rodent, primate (e.g., human and nonhuman primate), camelid, etc., or they can be recombinantly produced, e.g., chimeric, humanized, and/or in vitro-generated, e.g., by methods well known to those of skill in the art.

Examples of binding fragments encompassed within the term "antigen-binding fragment" of an antibody include, but are not limited to, (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment, which consists of a VH domain; (vi) a camelid or camelized heavy chain variable domain (VHH); (vii) a single chain Fv (scFv; see below); (viii) a bispecific antibody; and (ix) one or more fragments of an immunoglobulin molecule fused to an Fc region. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv)); see, e.g., Bird et al. (1988) *Science* 242: 423-26; Huston et al. (1988) *Proc. Natl. Acad. Sci. U.S.A.* 85:5879-83). Such single chain antibodies are also intended to be encompassed within the term "antigen-binding fragment" of an antibody. These fragments may be obtained using conventional techniques known to those skilled in the art, and the fragments are evaluated for function in the same manner as are intact antibodies.

The "antigen-binding fragment" can, optionally, further include a moiety that enhances one or more of, e.g., stability, effector cell function or complement fixation. For example, the antigen binding fragment can further include a pegylated moiety, albumin, or a heavy and/or a light chain constant region.

Other than "bispecific" or "bifunctional" antibodies, an antibody is understood to have each of its binding sites identical. A "bispecific" or "bifunctional antibody" is an artificial hybrid antibody having two different heavy/light chain pairs and two different binding sites. Bispecific antibodies can be produced by a variety of methods including fusion of hybridomas or linking of Fab' fragments. See, e.g., Songsivilai and Lachmann (1990) *Clin. Exp. Immunol.* 79:315-21; Kostelny et al. (1992) *J. Immunol.* 148:1547-53.

The phrase "protein" or "protein product" refers to one or more chains of amino acids. As used herein, the term "protein" is synonymous with "polypeptide" and, as is generally understood in the art, refers to at least one chain of amino acids liked via sequential peptide bonds. In certain embodiments, a "protein of interest" or a "polypeptide of interest" is a protein encoded by an exogenous nucleic acid molecule that has been transformed into a host cell. In certain embodiments, wherein the "protein of interest" is coded for by an exogenous DNA with which the host cell has been transformed, the nucleic acid sequence of the exogenous DNA determines the sequence of amino acids. In certain embodiments, a "protein of interest" is a protein encoded by a nucleic acid molecule that is endogenous to the host cell. In certain embodiments, expression of such an endogenous protein of interest is altered by transfecting a host cell with an exogenous nucleic acid molecule that may, for example, contain one or more regulatory sequences and/or encode a protein that enhances expression of the protein of interest. Methods and compositions of the present invention may be used to produce any protein of interest, including, but not limited to proteins having pharmaceutical, diagnostic, agricultural, and/or any of a variety of other properties that are useful in commercial, experimental and/or other applications. In addition, a protein of interest can be a protein therapeutic. Namely, a protein therapeutic is a protein that has a biological effect on a region in the body on which it acts or on a region of the body on which it remotely acts via intermediates. Examples of protein therapeutics are discussed in more detail below. In certain embodiments, proteins produced using methods and/or compositions of the present invention may be processed and/or modified. For example, a protein to be produced in accordance with the present invention may be glycosylated.

The present invention may be used to culture cells for the advantageous production of any therapeutic protein, such as pharmaceutically or commercially relevant enzymes, receptors, antibodies (e.g., monoclonal and/or polyclonal antibodies), Fc fusion proteins, cytokines, hormones, regulatory factors, growth factors, coagulation/clotting factors, antigen binding agents, etc. One of ordinary skill in the art will be aware of other proteins that can be produced in accordance with the present invention, and will be able to use methods disclosed herein to produce such proteins.

Expression Constructs and Generation of Recombinant Host Cells

The present invention uses recombinant host cells, e.g., prokaryotic or eukaryotic host cells, i.e., cells transfected with an expression construct containing a nucleic acid that encodes a polypeptide of interest. The phrase "animal cells" encompasses invertebrate, nonmammalian vertebrate (e.g., avian, reptile and amphibian), and mammalian cells. Nonlimiting examples of invertebrate cells include the following insect cells: *Spodoptera frugiperda* (caterpillar), *Aedes aegypti* (mosquito), *Aedes albopictus* (mosquito), *Drosophila melanogaster* (fruitfly), and *Bombyx mori* (silkworm/silk moth).

A number of mammalian cell lines are suitable host cells for recombinant expression of polypeptides of interest. Mammalian host cell lines include, for example, COS, PER.C6, TM4, VERO076, MDCK, BRL-3A, W138, Hep G2, MMT, MRC 5, FS4, CHO, 293T, A431, 3T3, CV-1, $C_3H_{10}T1/2$, Colo205, 293, HeLa, L cells, BHK, HL-60, FRhL-2, U937, HaK, Jurkat cells, Rat2, BaF3, 32D, FDCP-1, PC12, M1x, murine myelomas (e.g., SP2/0 and NS0) and C2C12 cells, as well as transformed primate cell lines, hybridomas, normal diploid cells, and cell strains derived from in vitro culture of primary tissue and primary explants. Any eukaryotic cell that is capable of expressing the polypeptide of interest may be used in the disclosed media design methods. Numerous cell lines are available from commercial sources such as the American Type Culture Collection (ATCC). In one embodiment of the invention, the cell culture, e.g., the large-scale cell culture, employs hybridoma cells. The construction of antibody-producing hybridoma cells is well known in the art. In one embodiment of the invention, the cell culture, e.g., the large-scale cell culture, employs CHO cells.

Alternatively, it may be possible to recombinantly produce polypeptides of interest in lower eukaryotes such as yeast, or in prokaryotes such as bacteria. Suitable yeast strains include *Saccharomyces cerevisiae*, *Schizosaccharomyces pombe*, *Kluyveromyces* strains, *Candida*, or any yeast strain capable of expressing polypeptide of interest. Suitable bacterial strains include *Escherichia coli, Bacillus subtilis, Salmonella typhimurium*, or any bacterial strain capable of expressing the polypeptide of interest. Expression in bacteria may result in formation of inclusion bodies incorporating the recombinant protein. Thus, refolding of the recombinant protein may be required in order to produce active or more active material. Several methods for obtaining correctly folded heterologous proteins from bacterial inclusion bodies are known in the art. These methods generally involve solubilizing the protein from the inclusion bodies, then denaturing the protein completely using a chaotropic agent. When cysteine residues are present in the primary amino acid sequence of the protein, it is often necessary to accomplish the refolding in an environment that allows correct formation of disulfide bonds (a redox system). General methods of refolding are disclosed in Kohno (1990) *Meth. Enzymol.* 185:187-95, EP 0433225, and U.S. Pat. No. 5,399,677.

The present invention uses constructs, in the form of plasmids, vectors, and transcription or expression cassettes, comprised of at least one polynucleotide encoding a polypeptide of interest. Vectors are capable of directing the expression of genes to which they are operably linked. Such vectors are referred to herein as "recombinant expression vectors" or "expression vectors." In general, expression vectors of utility in recombinant DNA techniques are often in the form of plasmids. In the present specification, "plasmid" and "vector" may be used interchangeably as the plasmid is the most common vector form. However, the invention is intended to include other forms of expression vectors that serve equivalent functions, including, but not limited to, viral vectors (e.g., replication defective retroviruses, modified alphaviruses, adenoviruses and adeno-associated viruses).

Constructs that are suitable for expression of proteins in animal cells are well known in the art. For example, polynucleotides may be operably linked to an expression control sequence such as those present in the pMT2 or pED expression vectors disclosed in, e.g., Kaufman et al. (1991) *Nuc. Acids Res.* 19:4485-90. Other suitable expression control sequences are found in vectors known in the art and include, but are not limited to: HaloTag™ pHT2, pACT, pBIND, pCAT®93, pCI, phRG, phRL (Promega, Madison, Wis.); pcDNA3.1, pcDNA3.1-E, pcDNA4/HisMAX, pcDNA4/HisMAX-E, pcDNA3.1/Hygro, pcDNA3.1/Zeo, pZeoSV2, pRc/CMV2, pBudCE4 pRc/RSV (Invitrogen, Carlsbad, Calif.); pCMV-3Tag Vectors, pCMV-Script® Vector, pCMV-Tag Vectors, pSG5 Vectors (Stratagene, La Jolla, Calif.); pDNR-Dual, pDNR-CMV (Clonetech, Palo Alto, Calif.); and pSMEDA (Wyeth, Madison, Wis.). General methods of expressing recombinant proteins are also known and are exemplified in, e.g., Kaufman (1990) *Meth. Enzymol.* 185: 537-66.

As defined herein "operably linked" means enzymatically or chemically ligated to form a covalent bond between the polynucleotide to be expressed and the expression control sequence in a manner that the encoded protein is expressed by the transfected host cell.

The recombinant expression constructs of the invention may carry additional sequences, such as regulatory sequences (e.g., sequences that regulate either vector replication (e.g., origins of replication, transcription of the nucleic acid sequence encoding the polypeptide (or peptide) of interest) or expression of the encoded polypeptide), tag sequences such as histidine, and selectable marker genes. The term "regulatory sequence" is intended to include promoters, enhancers and any other expression control elements (e.g., polyadenylation signals, transcription splice sites) that control transcription, replication or translation. Such regulatory sequences are described, for example, in Goeddel, *Gene Expression Technology: Methods in Enzymology*, Academic Press, San Diego, Calif. (1990). Those skilled in the art will recognize that the design of the expression vector, including the selection of regulatory sequences, will depend on various factors, including choice of the host cell and the level of protein expression desired. Preferred regulatory sequences for expression of proteins in mammalian host cells include viral elements that direct high levels of protein expression, such as promoters and/or enhancers derived from the FF-1a promoter and BGH poly A, cytomegalovirus (CMV) (e.g., the CMV promoter/enhancer), Simian virus 40 (SV40) (e.g., the SV40 promoter/enhancer), adenovirus (e.g., the adenovirus major late promoter (AdMLP)), and polyoma. Viral regulatory elements, and sequences thereof, are described in, e.g., U.S. Pat. Nos. 5,168,062; 4,510,245; and 4,968,615, all of which are incorporated by reference herein in their entireties.

Suitable vectors, containing appropriate regulatory sequences, including promoter sequences, terminator sequences, polyadenylation sequences, enhancer sequences, marker genes and other sequences as appropriate, may be either chosen or constructed. Inducible expression of proteins, achieved by using vectors with inducible promoter sequences, such as tetracycline-inducible vectors, e.g., pTet-On™ and pTet-Off™ (Clontech, Palo Alto, Calif.), may also be used in the disclosed method. For further details regarding expression vectors, see, for example, *Molecular Cloning: a Laboratory Manual* (2nd ed.) eds. Sambrook et al., Cold Spring Harbor Laboratory Press, Cold Spring Harbor, N.Y. (1989). Many known techniques and protocols for manipulation of nucleic acids, for example, in preparation of nucleic acid constructs, mutagenesis, sequencing, introduction of DNA into cells, gene expression, and analysis of proteins, are also described in detail in *Current Protocols in Molecular Biology* (2nd ed.) eds. Ausubel et al., Wiley & Sons, Alameda, Calif. (1992).

A polynucleotide inserted into an expression construct for producing a polypeptide of interest may encode any polypeptide that is capable of being expressed in the host cell used in the cell culture. Thus, the polynucleotide may encode full-length gene products, portions of full-length genes, peptides, or fusion proteins. Such polynucleotides may consist of genomic DNA or cDNA, and may be derived from any animal. Polynucleotides may be isolated from cells or organisms by methods well known in the art, e.g., PCR or RT-PCR, or may be produced by known conventional chemical synthesis methods. Such chemically synthetic polynucleotides may possess biological properties in common with natural polynucleotides, and thus may be employed as substitutes for natural polynucleotides.

Polypeptides may also be recombinantly produced by operably linking the polynucleotide encoding the polypeptide of interest to suitable control sequences in one or more insect expression vectors, such as baculovirus vectors, and employing an insect cell expression system. Materials and methods for baculovirus/Sf9 expression systems are commercially available in kit form (e.g., the MAXBAC® kit, Invitrogen, Carlsbad, Calif.).

Transfection of host cells, e.g., animal cells, with the expression construct may be achieved by numerous methods that are well known in the art. Cells may be either transiently transfected or stably transfected. Several different well-established methods exist for the delivery of molecules, particularly nucleic acids, into host cells, e.g., animal cells. Depending on the cell type, the desired transfection (i.e., transient or stable), and the specific experimental requirements, such as transfection of difficult cell lines or primary cells, the type of molecule transfected (genomic DNA, DNA, oligonucleotides), or the expression construct chosen, each transfer method possesses advantages and disadvantages known to those of skill in the art. Common transfection methods include, e.g., calcium phosphate precipitation, liposome mediated transfection, DEAE Dextran-mediated transfection, gene guns, electroporation, nanoparticle delivery, polyamines, episomes, and polyethylenimines. In addition, numerous transfection kits and reagents are commercially available from companies such as Invitrogen (VOYAGER™, LIPOFECTIN®), EMD Biosciences, San Diego, Calif. (GENEJUICE™), Qiagen, Germantown, Md. (SUPERFECT™), Orbigen, San Diego, Calif. (SAPPHIRE™), and many others known to those of skill in the art. Transfection protocols may also be found in *Basic Methods in Molecular Biology* ($2^{nd}$ ed.) eds. Davis et al., Appleton and Lange, Conn. (1994).

The present invention uses cell cultures, e.g., large-scale animal cell cultures, to produce large quantities of the polypeptide of interest. Methods for large-scale transient transfections are disclosed in *Large-scale Mammalian Cell Culture Technology* (Biotechnology and Bioprocessing Series) ed. Lubiniecki, Marcel Dekker, NY (1990); Kunaparaju et al. (2005) *Biotechnol. Bioeng.* 91:670-77; Maiorella et al. (1988) *Bio/Technology* 6:1406-10; Baldi et al., supra; Lan Pham et al., supra; Meissner et al., supra; Durocher et al., supra). In general, large-scale transient gene expression in mammalian cell cultures may employ any one of several common types of transfection modes, e.g., polyethylenimine, electric field pulse, CALFECTION™ or calcium phosphate, to achieve high transfection efficiency at desired scales or volumes, e.g., greater that 10 liters (Derouazi et al., supra; Rols et al. (1992) *Eur. J. Biochem.* 206(1): 115-21; Wurm and Bernard (1999) *Curr. Opin. Biotechnol.* 10(2):156-59; Schlaeger and Christensen (1999) *Cytotechnology* 30(1-3):71-83; Jordan et al. (1998) *Cytotechnology* 26(1):39-47; Lindell et al. (2004) *Biochim. Biophys. Acta* 1676(2):155-61). These large-scale cultures are generally grown in bioreactors, shakers, or incubators with stir plates, and may also be known as "spinner" or "suspension" cultures. Thus, as opposed to traditional transfections, in which cells are attached to plates or flasks, the disclosed methods generally use suspension cultures. Large-scale cell cultures are generally considered to be cell cultures that have a volume of greater than about 100 ml.

In some instances, cell lines expressing the polypeptide of interest may be first produced and then used to seed a large-scale cell culture. Stable cell lines that express a protein of interest may be produced by various well-known methods, including the methods used for transient transfection disclosed herein. In general, stable cell lines are produced by long-term growth and selection in a chemically defined media. For example, cells transfected (e.g., by calcium phosphate precipitation, or liposomal transfection) with a nucleic acid that encodes a polypeptide of interest may concomitantly be transfected with a vector carrying a neomycin resistance gene, which confers resistance to neomycin/geneticin (G418). The transfected cells are then grown in G418-containing media, and the surviving cells clonally expanded to produce a stably expressing cell line. Aliquots of this cell line may then be used to seed a large-scale culture and to produce large quantities of the protein of interest.

Transfecting cells requires the optimization of several variables, including cell-seeding density (e.g., about $1 \times 10^5$ to about $3 \times 10^6$ cells/ml culture), serum concentration (e.g., 0-10%), incubation temperature (e.g., about 20-38° C.), transfection vehicle or reagent (chemical or electric), culture volume (e.g., about 5 ml-20 liters), and incubation time (e.g., about 24-144 hours). For each cell type, optimal parameters will vary. However, commercial suppliers generally provide optimization guidelines for transfecting particular cell types, as do various references known to those of skill in the art that utilize transfection of the host cell chosen. These sources may be used to direct transfection of the chosen host cell, or may be used as a starting point from which simple trial and error may be used to provide optimum transfection parameters.

Cell Culture

Typical procedures for producing a polypeptide of interest include batch cultures and fed-batch cultures. Batch culture processes traditionally comprise inoculating a large-scale production culture with a seed culture of a particular cell density, growing the cells under conditions conducive to cell growth and viability, harvesting the culture when the cells reach a specified cell density, and purifying the expressed polypeptide. Fed-batch culture procedures include an additional step or steps of supplementing the batch culture with nutrients and other components that are consumed during the growth of the cells. One of ordinary skill in the art will recognize that the present invention can be employed in any system in which cells are cultured including, but not limited to, batch, fed-batch and perfusion systems. In certain preferred embodiments of the present invention, the cells are grown in fed-batch systems.

A persistent and unsolved problem with traditional cultures, e.g., batch and fed-batch cultures, is the production of metabolic waste products, which have detrimental effects on cell growth, viability, and production of expressed polypeptides. Two metabolic waste products that have particularly detrimental effects are lactate and ammonium, which are produced as a result of glucose and glutamine metabolism, respectively. In addition to the enzymatic production of ammonium as a result of glutamine metabolism, ammonium also accumulates in cell cultures as a result of nonmetabolic degradation over time.

Traditional media formulations, including commercially available media such as Ham's F10 (Sigma), Minimal Essential Medium ([MEM], Sigma), RPMI-1640 (Sigma), and Dulbecco's Modified Eagle's Medium ([DMEM], Sigma), contain relatively high levels of glucose and glutamine (the latter in comparison to other amino acids). Previously, these components were believed to be required in abundance since they are the primary metabolic energy sources for the cells. However, rapid consumption of these nutrients leads to the accumulation of lactate and ammonium as described above. Additionally, high initial levels of glucose and glutamine, and the subsequent accumulation of lactate and ammonium, result in high osmolarity, a condition that by itself is often detrimental to cell growth, cell viability and the production of polypeptides. The rationally designed medium disclosed herein may be modified to decrease the accumulation of harmful metabolic products. Such modifications may be found in, e.g., U.S. Published Patent Application Nos. 2005/0070013 (restricted glucose feeding) and 2006/0121568 (modifications of amino acid content and ratios) (both of which are hereby incorporated by reference herein in their entireties).

Rational Media Design and Formulations

Traditional media formulations begin with a relatively low level of total amino acids in comparison with the media formulations of the present invention. For example, DME-F12 (a 50:50 mixture of Dulbecco's Modified Eagle's medium and Ham's F12 medium) has a total amino acid content of 7.29 mM, and the traditional cell culture medium known as RPMI-1640 has a total amino acid content of 6.44 mM (see e.g., Morton (1970) *In Vitro* 6:89-108; Ham (1965) *Proc. Nat. Acad. Sci. U.S.A.* 53:288-93; Moore et al. (1967) *J. Am. Medical Assn.* 199:519-24, all incorporated by reference herein). More recent media formulations (such as the media disclosed in U.S. Published Patent Application No. 2006/0121568) contain higher levels of amino acids and nutrients. Traditional formulations, however, are not based on actual calculated cell requirements, which include cell growth, cell maintenance, and, for cell cultures used to produce recombinant polypeptides, production requirements. Using these variables, provided herein are methods of determining media formulations with much higher, and yet nontoxic, concentrations of total amino acids.

The cell culture media formulations, e.g., the large-scale cell culture media formulations, described herein, when used in accordance with, e.g., other culturing steps described herein, and with, e.g., modifications such as those found in, e.g., U.S. Published Patent Application No. 2006/0121568, optimize cell density and polypeptide titer. An amino acid concentration of the media formulations described herein is based on the concentration of the amino acid(s) required for: 1) cell mass; 2) cell maintenance; and 3) polypeptide production. In one embodiment of the invention, a cell culture medium contains a concentration of the amino acid(s) that is calculated for use in cell mass, a concentration of the amino acid(s) that is calculated for use in cell maintenance, and a concentration of the amino acid(s) that is calculated for incorporation into the polypeptide of interest. In another embodiment of the invention, a cell culture medium contains a concentration, A, of an amino acid that is represented by the formula $A=[(M*X)+(N*P)+(Y*M*X)]*F$, wherein X is the concentration of the amino acid that is used per unit of cell mass, P is the concentration of the amino acid that is used for incorporation into the polypeptide of interest per unit of polypeptide titer, M is the multiplier for the desired cell mass (i.e., the desired peak units of cell mass), N is the multiplier for the desired concentration of the polypeptide of interest (i.e., desired or target polypeptide titer), Y is the cell maintenance factor; and F is the baseline factor.

The concentration, P, of the amino acid that is used for incorporation into the polypeptide of interest per unit of polypeptide titer in the formula above is based on the primary structure of the recombinant protein, i.e., the amino acid content of the polypeptide. Thus, P will vary based on the polypeptide of interest that is to be produced by the large-scale cell culture. P may then be converted to the amino acid requirement for the target concentration of the polypeptide of interest using N, the multiplier for the desired concentration of the polypeptide of interest (i.e., desired or target polypeptide titer). In some representative examples of the invention below, the basic unit of polypeptide titer is 1 g/L. In Table 1, below, which contains a representative calculation using the formula supplied herein, the amino acid concentration of the cell culture medium that is required for the polypeptide of interest at a titer of 10 g/L (column 4) is determined by multiplying the concentration, P, of the amino acid required for 1 g/L (column 2) by the multiplier, N, wherein N=10.

TABLE 1

Representative Determination of Baseline-Adjusted Amino Acid Concentration Required For Target Titer of 10 g/L Antibody at a Desired Cell Mass, Where Desired Cell Mass Is Represented by Desired Peak Cell Density of $15 \times 10^6$ cells/ml

| 1 Amino Acid (AA) | 2 (P) AA Concentration Required For Initial Antibody Titer of 1 g/L mM | 3 (X) AA Concentration Required for Cell Mass Represented by Cell Density of $10^6$ cells/ml mM | 4 (P × N) Total AA Concentration Required for Target Antibody Titer of 10 g/L (N = 10) Column 2 × 10 mM | 5 (X × M) Total AA Concentration Required for Desired Peak Cell Density of $15 \times 10^6$ cells/ml (M = 15) Column 3 × 15 mM | 6 (X × M × Y) Total AA Concentration Required for Cell Maintenance (Y = 100%) or (Y = 1) Column 5 × 100% mM | 7 Calculated Total AA Concentration Required for Target Antibody Titer and Desired Peak Cell Density (Column 4 + 5 + 6) mM | 8 (A) (Column 7 × F) Baseline-Adjusted AA Concentration Required for Target Antibody Titer and Desired Peak Cell Density (F = 1.3) Column 7 × 1.3 mM |
|---|---|---|---|---|---|---|---|
| ALA | 0.41 | 0.30 | 4.08 | 4.56 | 4.56 | 13.20 | 17.17 |
| ARG | 0.17 | 0.16 | 1.73 | 2.38 | 2.38 | 6.50 | 8.45 |
| ASN | 0.26 | 0.15 | 2.62 | 2.23 | 2.23 | 7.08 | 9.21 |
| ASP | 0.29 | 0.29 | 2.87 | 4.36 | 4.36 | 11.59 | 15.07 |
| CYS | 0.19 | 0.09 | 1.88 | 1.42 | 1.42 | 4.73 | 6.14 |
| GLU | 0.40 | 0.16 | 4.00 | 2.33 | 2.33 | 8.67 | 11.26 |
| GLN | 0.39 | 0.29 | 3.87 | 4.40 | 4.40 | 12.67 | 16.47 |
| GLY | 0.47 | 0.25 | 4.72 | 3.80 | 3.80 | 12.33 | 16.02 |
| HIS | 0.16 | 0.07 | 1.59 | 1.07 | 1.07 | 3.72 | 4.83 |
| ILE | 0.14 | 0.16 | 1.43 | 2.33 | 2.33 | 6.10 | 7.93 |
| LEU | 0.49 | 0.25 | 4.88 | 3.80 | 3.80 | 12.49 | 16.24 |
| LYS | 0.52 | 0.24 | 5.20 | 3.55 | 3.55 | 12.31 | 16.00 |
| MET | 0.10 | 0.06 | 0.97 | 0.86 | 0.86 | 2.69 | 3.50 |
| PHE | 0.23 | 0.12 | 2.34 | 1.78 | 1.78 | 5.89 | 7.65 |
| PRO | 0.59 | 0.16 | 5.94 | 2.33 | 2.33 | 10.61 | 13.79 |
| SER | 0.97 | 0.34 | 9.73 | 5.11 | 5.11 | 19.96 | 25.94 |
| THR | 0.68 | 0.20 | 6.80 | 3.04 | 3.04 | 12.88 | 16.75 |
| TRP | 0.16 | 0.04 | 1.64 | 0.56 | 0.56 | 2.75 | 3.58 |
| TYR | 0.35 | 0.12 | 3.48 | 1.78 | 1.78 | 7.03 | 9.14 |
| VAL | 0.74 | 0.23 | 7.36 | 3.50 | 3.50 | 14.36 | 18.67 |
| Total (mM) | 7.71 | 3.68 | 77.13 | 55.21 | 55.21 | 187.55 | 243.82 |

The multiplier N may be calculated, e.g., by multiplying the integrated viable cell density (IVC) by the specific productivity (qp) of a particular cell line (N=IVC*qp). For example, if the seed density of a particular cell line is $0.8 \times 10^6$ cells/ml, the cell density at day 6 and day 10 is $15 \times 10^6$ cells/ml, and the cell density at day 18 is $11 \times 10^6$ cells/ml (i.e., 73% of the value at days 6 and 15), then the IVC=$211 \times 10^6$ (cells/ml)*day (i.e., [(0.8+15)/2]*6 days+[(15+15)/2]*4 days+[(15+11)/2]*8 days). If the average specific productivity (qp) of the chosen cell line is, e.g., 47 µg/$10^6$ cells/day, then N=10 g/L at day 18 (i.e., $211 \times 10^6$ (cells/ml)*day×47 µg/$10^6$ cells/day). One of skill in the art will realize that these calculations may be performed with any cell line, or that N may be estimated based on cell characteristics and origin. Alternatively, the multiplier N need not be calculated from IVC and qp, and may simply be a reasonable target titer for a particular cell culture. A prophetic example, describing the calculation of IVC and qp, and the further selection of reasonable N and M values, is provided as Example 5 (below).

As used herein, "cell mass," "cell density," and the like refer to a collection of cells. For example, a cell mass can refer to a cell pellet. As used herein, "desired cell mass" and the like refers to a collection of cells, e.g., a cell pellet, that a practitioner desires to obtain in a cell culture. As used herein, "unit of cell mass" and the like reflects a number of ways of representing cell mass, e.g., cell number, cell density, cell volume, packed cell volume, dry cell weight, etc. One skilled in the art will know which is the most convenient or appropriate way of representing a unit of cell mass, etc., for a particular experimental condition. One skilled in the art will also understand that, depending on the unit of cell mass, M, the multiplier for desired cell mass, i.e., the desired peak units of cell mass, will be represented by either desired peak cell numbers, desired peak cell density, desired peak cell volume, desired peak packed cell volume, desired peak dry weight, etc.

In one embodiment of the invention, the unit of cell mass is represented by cell density and the desired cell mass is represented by desired peak cell density. In another embodiment, the unit of cell mass is represented by dry cell weight or mass. The dehydrated cell mass consists essentially of all proteins, carbohydrates, lipids, and nucleic acids present in that cell mass. Thus, the concentration, X, of an amino acid can be determined experimentally, by first spinning a known number of cells to a cell pellet, drying the cell pellet, and subsequently exposing the dried pellet to acid-hydrolysis, thereby lysing the cellular proteins of the cell pellet to individual amino acids, which may then be quantified by an amino acid analyzer (see, e.g., Example 1). This provides the amino acid concentration, X, of a given number of cells, which may then be converted to the amino acid requirement for the desired peak cell density using M, the multiplier for the desired peak cell density. In Table 1, the total amino acid concentration of the cell culture medium that is required for the desired peak cell density of $15 \times 10^6$ cells/ml (column 5) is determined by multiplying the concentration, X, of the amino acid required for $10^6$ cells/ml (column 3) by the multiplier, M, wherein M=15. Thus, in some representative examples of the invention, the unit of cell mass is $10^6$ cells/ml. Alternatively, e.g., for an amino acid known to be susceptible to degradation, the concentration, X, of the amino acid that is used in the formula above may be determined from literature values, e.g., Nyberg et al. (1999) *Biotechnol. Bioeng.* 62:324-35; Nadeau et al. (2000) *Metab. Eng.* 2:277-92; and Bonarius (1996) *Biotech-* nol. Bioeng. 50:299-318, or the methods disclosed in such publications or similar publications known in the art.

When the multiplier M for desired cell mass is represented desired peak cell density, M may be chosen as, e.g., the peak density of a particular cell line, by the density at which the productivity of the cell line is maximized, or by the predicted density for the cell line at a particular time period based on the specific growth rate.

The amino acid concentration of the cell culture medium that is required for cell maintenance, Y, is a percentage of the amino acid concentration required for the desired cell mass, e.g., desired peak cell density. In one embodiment of the invention, the maintenance requirement ranges from 0% to 300% of the desired cell mass requirement, which provides sufficient nutrients for cell use without risk of nutrient-induced toxicity. In another embodiment of the invention, the maintenance requirement ranges from 0% to 150% of the desired cell mass requirement, which provides sufficient nutrients for cell use without risk of nutrient-induced toxicity. The maintenance requirement increases as culture duration increases (e.g., 100-150% maintenance for a 21 day culture). In Table 1, the amino acid concentration of the cell culture medium that is required for cell maintenance (column 6) is determined by multiplying the amino acid concentration required for the desired peak cell density (column 5) by the cell maintenance factor, Y, which in this representative example is 100%, in order to allow an extended culture period. The maintenance factor, Y, will differ for different cells (and different cell lines) depending on the unique metabolic demands of the cells in culture. Further, the maintenance requirements for cells in culture will also differ due to the variability in processes, e.g., inoculation density, culture duration, time of temperature shift, etc. As an initial guideline, one may provide, e.g., 0% maintenance (daily) for cultures at days 0 to 5, 3% to 5% maintenance (daily) for cultures at days 6 to 10, and 7% to 10% maintenance (daily) for cultures at days 11 to 21. For a process greater than 21 days, cultures may be provided 2% to 5% maintenance (daily) for those additional days. One of ordinary skill in the art will realize that adjusting the maintenance factor, Y, to optimize density and titer, is merely a matter of routine trial and error. Adjusting amino acid concentration according to the cell maintenance requirement is important for increased viability and productivity of the cell culture, and thus is an important aspect of the present invention. For example, adjusting amino acid concentration according to the cell maintenance requirement enables the cell culture to sustain greater cell density, cell viability, and to produce higher polypeptide titer (see, e.g., Example 6).

Once the amino acid requirements of desired: 1) cell mass (column 5); 2) cell maintenance (column 6); and 3) polypeptide production for the target titer (column 4) are determined, the calculated total amino acid concentration of the target cell culture may be obtained. In Table 1, the calculated total amino acid concentration of the cell culture medium that is required for the target cell culture (column 7), is determined by adding the amino acid concentration of the cell culture medium that is required for the polypeptide of interest at a titer of 10 g/L (column 4), the amino acid concentration of the cell culture medium that is required for the desired peak cell density of $15 \times 10^6$ cells/ml (column 5), and the amino acid concentration of the cell culture medium that is required for a selected level of cell maintenance (column 6).

Once the calculated total amino acid concentration of the cell culture medium that is required for the target cell culture is obtained as described above, the value is adjusted to a desired cell culture medium amino acid concentration, A, by a baseline factor, F, which allows for the driving force of amino transfer, e.g., the extra amino acids required for mass transfer, the extra amino acids required to drive transport across cell membrane, etc. This adjusted value, A, is referred to herein as the "baseline-adjusted amino acid concentration" or "optimized concentration." The baseline-adjusted amino acid concentration, A, represents the cumulative total amount of an amino acid(s) that will be delivered to the culture, expressed relative to the final volume of the culture, which includes the volume of the starting medium, plus the volume of any feeds for perfusion or fed-batch culture(s). Adjusting the total amino acid concentration to the baseline-adjusted amino acid concentration is an important aspect of the invention because it allows higher cell viability, cell density, and polypeptide titers (see, e.g., Example 6).

The baseline factor, F, which increases the calculated total amino acid concentration of the cell culture medium by up to 200%, ranges from 1 (0% increase) to 3 (200% increase). In one embodiment of the invention, the range for F is between 1 and 1.5. In another embodiment of the invention, a value of F below 1 may be offset by modifying the calculated total amino acid concentration of the cell culture medium (Table 1, column 7), which may be achieved by modifying the amino acid concentration required for desired cell mass, the amino acid concentration required for cell maintenance, and/or the amino acid concentration required for incorporation into the polypeptide of interest. For example, a baseline factor of 0.5 may be offset by increasing the calculated total amino acid concentration of the cell culture medium by, e.g., a factor of two (or more), which may be achieved by varying M, X, N, P and/or Y. In Table 1, the baseline-adjusted amino acid concentration, A, of the cell culture medium that is required for the target titer and desired peak cell density (column 8), is determined by multiplying the calculated total amino acid concentration of the cell culture medium (column 7), by the baseline factor, F, which in the representative example of Table 1 is 1.3 (corresponding to a 30% increase over the calculated total amino acid concentration of the cell culture medium).

Medium containing the baseline-adjusted concentration, A, of an amino acid is referred to herein as the "desired cell culture medium." Thus, the "desired cell culture medium" represents a goal medium that contains the baseline-adjusted concentration, A. This medium comprises at least one amino acid concentration determined by the above formula. Preferably the desired cell culture medium contains more than one amino acid concentration determined by the above formula. More preferably, the desired cell culture medium contains at least twelve adjusted amino acid concentrations, e.g., an adjusted concentration of arginine, histidine, isoleucine, leucine, lysine, phenylalanine, proline, serine, threonine, tryptophan, tyrosine, and valine, determined by the above formula. It will be understood by one of skill in the art that the baseline-adjusted amino acid concentration, A, in the desired cell culture medium may be achieved by any number of means, including, but not limited to, individually adding the amino acid(s), adding peptone or other protein hydrolysates, and/or by adding another concentrated cell culture medium (e.g., a feeding cell culture medium (or medium mix, e.g., a medium powder)) to a starting cell culture medium (or starting cell culture medium mix, e.g., a medium powder). One of skill in the art will understand that the addition of peptone (or other protein hydrolysate) may be directed by the amino acid contents of the particular peptone product of choice, or by determining the amino acid concentration provided by a particular peptone, e.g., in general, 5 g/L peptone provides a concentration of about 40 mM to about 50 mM total amino acids.

The amino acid concentration in the desired cell culture medium is based on at least one baseline-adjusted amino acid concentration, A, determined by the inventive formula disclosed herein; however, that concentration, as well as other concentrations of amino acids in the desired cell culture medium, may be varied from the baseline-adjusted amino acid concentration(s) due to the influence of several factors. For example, certain amino acids may be produced during culturing, and thus may be kept at a low level. Other amino acids may be varied based on published values (see, e.g., U.S. Published Patent Application No. 2006/0121568). Further, some amino acids, e.g., methionine, may be consumed at a greater rate by particular cell types, and thus should be added in excess. Yet other amino acids, such as proline, provide a driving force for cell growth and polypeptide production (see Example 4), and these amino acids should be provided, in some cases, at a greater amount than determined by the above inventive formula. In addition, one may modify the baseline-adjusted amino acid concentration if the concentration obtained using the above formula is considered to be toxic (e.g., consideration of the levels of serine, tyrosine, methionine and valine). It is within the knowledge of one of skill in the art, upon obtaining the baseline-adjusted amino acid concentration, A, of an amino acid(s) for use in the desired cell culture medium, to vary the baseline-adjusted amino acid concentration based on factors such as those noted herein.

Additional media components, for example, vitamins, salts, glucose, elements, may be calculated from (or based on) various sources, e.g., U.S. Published Patent Application Nos. 2005/0070013 and 2006/0121568. Further, the baseline-adjusted amino acid concentration, A, of an amino acid obtained using the above formula may be modified to provide a particular ratio in relation to another amino acid (e.g., the ratio of glutamine to asparagine) or to fall within a desired combined concentration (e.g., the combined concentration of glutamine and asparagine). For example, it is known that a high asparagine, low glutamine medium, combined with temperature shift, enables uptake of lactate, thereby detoxifying a cell culture (U.S. Published Patent Application No. 2006/0121568). Thus, one may wish to modify the baseline-adjusted concentration, A, of glutamine and/or asparagine, in order to obtain an optimum ratio.

It will be noted from the representative example in Table 1 that the combined concentration of the baseline-adjusted amino acid concentrations for use in the desired cell culture medium is high, i.e., over 243 mM. Thus, disclosed herein is the finding that a high concentration of amino acids may be used in a desired cell culture medium without toxicity or titer detriment if that concentration is based upon the calculated amino acid requirements for a target cell density and polypeptide titer. In one embodiment of the invention, the combined concentration of amino acids in the desired cell culture medium is between about 120 mM and about 250 mM. In other embodiments, the combined concentration of amino acids in the desired cell culture medium is greater than about 250 mM, e.g., about 260, 270, 280, 290, 300, 310, 320, 330, 340, 350, 360, 370, 380, 390, 400, 410, 420, 430, 440, 450, 460, 470, 480, 490, 500 or 510 mM, or any intermediate value.

The above-identified baseline-adjusted concentration, A, of an amino acid that is used in a desired cell culture medium, may be used in batch, fed-batch, and perfusion cultures. When used in batch culture, the initial concentration of the amino acid used in the desired cell culture medium is the baseline-adjusted amino acid concentration, A. When used in fed-batch or perfusion cultures, the baseline-adjusted amino acid concentration, A, represents the cumulative total amount of an amino acid(s) that will be delivered to the culture, which includes the volume of the starting medium plus the volume of all feeds. Thus, for fed-batch cultures, which use either continuous feeds (e.g., feeds on days 3-21) or periodic feeds (e.g., feeds every 2-3 days), the starting medium is engineered to contain a starting concentration of the amino acid, B, according to the formula $B=[A-(Z*V)]/(1-V)$, wherein Z is the concentration of the amino acid in the feeding cell culture medium, and V is the volume of the feeding culture medium as a proportion of the desired cell culture medium volume. A representative example of the calculations required to obtain the starting amino acid concentration, B, is provided in Table 2, below. In Table 2, some baseline-adjusted amino acid concentrations, A (column 2), are converted to the starting media amino acid concentration, B (column 5), based on a 17% feed volume (V=17%), and the feeding medium amino acid concentration, Z (column 4). In this example, several baseline-adjusted amino acid concentrations, A (column 2), and starting amino acid concentrations, B (column 5), are modified to the values shown in bold in columns 3 and 6. Modification of asparagine, aspartic acid, glutamine, and cysteine concentrations was based on the concentrations suggested by U.S. Published Patent Application No. 2006/0121568; methionine was adjusted by 50% to compensate for its consumption at a higher amount than predicted; alanine, glutamic acid and glycine are produced by the cultures (and thus kept at a low level); and serine, tyrosine, and valine concentrations were decreased to nontoxic levels. It will therefore be understood that the starting amino acid concentration, B, may be based on either the baseline-adjusted amino acid concentration, A, or on the modified baseline-adjusted amino acid concentration.

One of skill in the art will appreciate that the feeding medium used to obtain the desired cell culture medium during fed-batch and perfusion cell culturing should be as highly concentrated as possible in order to avoid overflow in the container in which the culture is carried out (e.g., a bioreactor or shaker flask) and to avoid diluting the media components. In the example set forth in Table 2, a preferred feeding media is denoted "Feed Medium," and the amino acid concentrations, Z, of the Feed Medium are set forth in column 4. However, any highly concentrated feeding medium, or any method of providing highly concentrated amino acids to the starting cell culture medium may be used, as long as the desired baseline-adjusted amino acid concentration, A, will be achieved in the target volume. Such methods of providing highly concentrated amino acids to a cell culture are commonly used and well known to one of skill in the art.

It will be understood by one of skill in the art that the starting concentration of the amino acid, B, in the starting cell culture medium may be achieved by any number of means, including, but not limited to, individually adding the amino acid(s), adding peptone and/or other protein hydrolysate, and/or adding another concentrated culture medium (or medium mix, e.g., a medium powder) to the starting cell culture medium (or starting cell culture medium mix, e.g., a medium powder). It will also be understood by one of skill in the art that the concentration of the amino acid, Z, in the feeding cell culture medium may be achieved by any number of means, including, but not limited to, individually adding the amino acid(s), adding peptone and/or other protein hydrolysate, and/or adding another concentrated culture medium (or medium mix, e.g., a medium powder) to the feeding cell culture medium (or feeding cell culture medium mix, e.g., a medium powder).

It will be noted from the representative example in Table 2 that the combined concentration of amino acids for use in the starting cell culture medium is high, i.e., over 125 mM. Thus, disclosed herein is the finding that a high concentration of amino acids may be used without toxicity or titer detriment in a starting cell culture medium if the starting amino acid concentration is based upon the calculated amino acid requirements for a desired peak cell density and a desired polypeptide titer. In one embodiment of the invention, the combined concentration of amino acids is between about 70 mM and about 510 mM. In one embodiment of the invention, the combined concentration of amino acids is between about 120 mM and about 350 mM. In another embodiment of the invention, the combined concentration of amino acids in the starting cell culture medium is between about 70 mM and about 140 mM. In another embodiment of the invention, the combined concentration of amino acids in the starting cell culture medium is greater than about 140 mM.

TABLE 2

Representative Determination of Starting Amino Acid Concentration For A Target Titer of 10 g/L Antibody, a Desired Peak Cell Density of $15 \times 10^6$ cells/ml, and a 17% Feed

| 1 Amino Acid (AA) | 2 (A) Baseline-Adjusted AA Concentration Required for Target Titer and Desired Peak Cell Density mM | 3 Modification of Baseline-Adjusted AA Concentration Required for Target Titer and Desired Peak Cell Density mM | 4 (Z) Feed Medium AA Concentration mM | 5 (B) Starting AA Concentration Required For Target Titer and Desired Peak Cell Density (V = 17%) mM | 6 Modified Starting AA Concentration Required For Target Titer and Desired Peak Cell Density mM |
|---|---|---|---|---|---|
| ALA | 17.17 | 0.20 | 6.4 | −1.07 | 0.2 |
| ARG | 8.45 | 8.45 | 35.13 | 2.99 | 2.99 |
| ASN | 9.21 | 24.00 | 56 | 17.45 | 17.45 |
| ASP | 15.07 | 1.70 | 16 | −1.23 | 1.7 |
| CYS | 6.14 | 0.40 | 0 | 0.48 | 0.4 |
| GLU | 11.26 | 0.20 | 6.4 | −1.07 | 0.2 |
| GLN | 16.47 | 4.00 | 0 | 4.82 | 4.2 |
| GLY | 16.02 | 4.00 | 6.4 | 3.51 | 3.51 |
| HIS | 4.83 | 4.83 | 11.2 | 3.53 | 3.53 |
| ILE | 7.93 | 7.93 | 28.82 | 3.65 | 3.65 |
| LEU | 16.24 | 16.24 | 41.53 | 11.06 | 11.06 |
| LYS | 16.00 | 16.00 | 32 | 12.72 | 12.72 |
| MET | 3.50 | 5.25 | 12.8 | 3.71 | 3.71 |
| PHE | 7.65 | 7.65 | 16 | 5.94 | 5.94 |
| PRO | 13.79 | 13.79 | 19.2 | 12.68 | 12.68 |
| SER | 25.94 | 25.94 | 48.15 | 21.39 | 10.2 |
| THR | 16.75 | 16.75 | 25.6 | 14.94 | 14.94 |
| TRP | 3.58 | 3.58 | 5.11 | 3.27 | 3.27 |
| TYR | 9.14 | 9.14 | 12.75 | 8.40 | 5.2 |
| VAL | 18.67 | 18.67 | 25.6 | 17.25 | 10.2 |
| Total (mM) | 243.82 | | 405.09 | | 127.73 |

As shown in Table 3A and Table 3B, the determination of the baseline-adjusted amino acid concentration of an amino acid, A, used in a desired cell culture medium, and the determination of the starting amino acid concentration, B, used in the starting cell culture medium, may be calculated for any desired target polypeptide titer and desired peak (target) cell density. The desired peak cell density of the large-scale culture ranges from about 3 to about $40 \times 10^6$ cells/mL for fed-batch culture. In one embodiment of the invention, the desired peak cell density ranges from about 5 to about $20 \times 10^6$ cells/mL. The target titer of the large-scale culture ranges from about 3 to about 25 g/L. In yet another embodiment of the invention, the target titer of the large-scale culture ranges from about 5 to about 20 g/L. For example, in Table 3, desired peak cell density ranges from 10 to $15 \times 10^6$ cells/mL, and target titer varies from 3 to 10 g/L.

TABLE 3A

Representative Examples of Baseline-Adjusted Amino Acid Concentrations, A, for Various Target Titers (As Represented by a Multiplier for Target Polypeptide Titer, N) and Desired Peak Cell Densities (As Represented by a Multiplier for Desired Peak Cell Density, M).

| | A | | |
|---|---|---|---|
| | N = 10 M = 15 | N = 5 M = 12.5 | N = 3 M = 10 |
| | Amino Acid Concentration | | |
| | mM | mM | mM |
| ALA | 17.2 | 12.5 | 9.50 |
| ARG | 8.5 | 6.3 | 4.81 |
| ASN | 9.2 | 6.5 | 4.89 |
| ASP | 15.1 | 11.3 | 8.68 |
| CYS | 6.1 | 4.3 | 3.20 |

TABLE 3A-continued

Representative Examples of Baseline-Adjusted Amino Acid Concentrations, A, for Various Target Titers (As Represented by a Multiplier for Target Polypeptide Titer, N) and Desired Peak Cell Densities (As Represented by a Multiplier for Desired Peak Cell Density, M).

| | A | | |
|---|---|---|---|
| | N = 10 M = 15 | N = 5 M = 12.5 | N = 3 M = 10 |
| | Amino Acid Concentration | | |
| | mM | mM | mM |
| GLU | 11.3 | 7.7 | 5.60 |
| GLN | 16.5 | 12.1 | 9.14 |
| GLY | 16.0 | 11.3 | 8.43 |

TABLE 3A-continued

Representative Examples of Baseline-Adjusted Amino Acid Concentrations, A, for Various Target Titers (As Represented by a Multiplier for Target Polypeptide Titer, N) and Desired Peak Cell Densities (As Represented by a Multiplier for Desired Peak Cell Density, M).

| | A | | |
|---|---|---|---|
| | N = 10<br>M = 15 | N = 5<br>M = 12.5 | N = 3<br>M = 10 |
| | Amino Acid Concentration | | |
| | mM | mM | mM |
| HIS | 4.8 | 3.3 | 2.46 |
| ILE | 7.9 | 6.0 | 4.60 |
| LEU | 16.2 | 11.4 | 8.50 |
| LYS | 16.0 | 11.1 | 8.18 |
| MET | 3.5 | 2.5 | 1.87 |
| PHE | 7.7 | 5.4 | 3.99 |
| PRO | 13.8 | 8.9 | 6.36 |
| SER | 25.9 | 17.4 | 12.66 |
| THR | 16.8 | 11.0 | 7.93 |
| TRP | 3.6 | 2.3 | 1.61 |
| TYR | 9.1 | 6.1 | 4.43 |
| VAL | 18.7 | 12.4 | 8.94 |
| Total | 243.8 | 169.8 | 125.8 |

TABLE 3B

Representative Examples of Starting Media Amino Acid Concentrations, B, for Various Target Titers (As Represented by a Multiplier for Target Polypeptide Titer, N) and Desired Peak Cell Densities (As Represented by a Multiplier for Desired Peak Cell Density, M); Starting Media Amino Acid Concentrations Were Determined by Subtracting Feed and Other Modifications from Baseline-Adjusted Amino Acid Concentrations

| | B | | |
|---|---|---|---|
| | N = 10<br>M = 15 | N = 5<br>M = 12.5 | N = 3<br>M = 10 |
| | Amino Acid Concentration | | |
| | mM | mM | mM |
| ALA | 0.2 | 0.2 | 0.20 |
| ARG | 3.0 | 1.9 | 1.68 |
| ASN | 17.4 | 14.6 | 10.77 |
| ASP | 1.7 | 1.7 | 1.70 |
| CYS | 0.4 | 0.4 | 0.40 |
| GLU | 0.2 | 0.2 | 0.20 |
| GLN | 4.0 | 4.0 | 4.00 |
| GLY | 3.5 | 3.6 | 3.75 |
| HIS | 3.5 | 2.2 | 1.56 |
| ILE | 3.6 | 2.5 | 2.10 |
| LEU | 11.1 | 6.9 | 5.09 |
| LYS | 12.7 | 7.9 | 5.73 |
| MET | 3.7 | 2.4 | 1.78 |
| PHE | 5.9 | 3.8 | 2.75 |
| PRO | 12.7 | 7.4 | 5.04 |
| SER | 10.2 | 10.2 | 9.00 |
| THR | 14.9 | 8.8 | 6.10 |
| TRP | 3.3 | 1.8 | 1.24 |
| TYR | 5.2 | 5.1 | 3.58 |
| VAL | 10.2 | 10.4 | 7.22 |
| Total | 127.5 | 95.9 | 73.89 |

Using the formula to determine baseline-adjusted amino acid concentration(s) and to develop desired cell culture media formulations for large-scale polypeptide production, the inventors have identified several criteria that result in high titer and high cell density cultures. The criteria for producing a titer higher than 5 g/L, which are represented by the values shown in Table 4, include, but are not limited to, one or more of the following: greater than or equal to about 3 mM tyrosine; between about 7 mM and about 30 mM proline; between about 7 mM and about 30 mM valine; between about 7 mM and about 30 mM leucine; between about 7 mM and about 30 mM threonine; between about 7 mM and about 30 mM lysine; a combined concentration of leucine, lysine, proline, threonine and valine that is between about 35 mM and about 150 mM; a combined concentration of leucine, lysine, threonine and valine that is between about 60% to about 80% of the total essential amino acids in the desired cell culture medium; a combined concentration of the essential amino acids in the desired cell culture medium that is between about 30% to about 50% of the total amino acids in the desired cell culture medium; and/or a combined concentration of total amino acids between about 75 mM and about 510 mM.

TABLE 4

Representative Examples of the Amino Acid Content and Relationships For Rationally Designed Media for Various Target Titers and Desired Peak Cell Densities (as noted above, the basic unit of polypeptide titer is 1 g/L, and the basic unit of cell mass is $10^6$ cells/ml).

| Amino Acid | N = 5<br>M = 10<br>Y = 0<br>F = 1<br>(mM) | N = 10<br>M = 10<br>Y = 1<br>F = 1.3<br>(mM) | N = 15<br>M = 10<br>Y = 1<br>F = 1.3<br>(mM) | N = 15<br>M = 20<br>Y = 1<br>F = 1.3<br>(mM) | N = 15<br>M = 30<br>Y = 1.5<br>F = 1.3<br>(mM) |
|---|---|---|---|---|---|
| ALA | 5.08 | 13.21 | 15.86 | 23.77 | 37.62 |
| *ARG* | *2.46* | *6.39* | *7.51* | *11.65* | *18.88* |
| ASN | 2.80 | 7.28 | 8.98 | 12.85 | 19.62 |
| ASP | 4.34 | 11.29 | 13.15 | 20.71 | 33.94 |
| CYS | 1.89 | 4.91 | 6.14 | 8.60 | 12.91 |
| GLU | 3.55 | 9.24 | 11.84 | 15.89 | 22.96 |
| GLN | 4.87 | 12.66 | 15.18 | 22.80 | 36.15 |
| GLY | 4.90 | 12.73 | 15.79 | 22.39 | 33.93 |
| *HIS* | *1.50* | *3.91* | *4.94* | *6.78* | *10.01* |
| *ILE* | *2.27* | *5.91* | *6.84* | *10.88* | *17.96* |
| LEU | 4.98 | 12.94 | 16.12 | 22.71 | 34.25 |
| LYS | 4.97 | 12.92 | 16.30 | 22.46 | 33.23 |
| *MET* | *1.06* | *2.76* | *3.39* | *4.88* | *7.50* |
| PHE | 2.35 | 6.11 | 7.63 | 10.71 | 16.09 |
| PRO | 4.53 | 11.77 | 15.63 | 19.67 | 26.75 |
| SER | 8.27 | 21.51 | 27.83 | 36.70 | 52.21 |
| THR | 5.43 | 14.11 | 18.53 | 23.81 | 33.04 |
| *TRP* | *1.19* | *3.10* | *4.16* | *5.13* | *6.82* |
| TYR | 2.92 | 7.60 | 9.87 | 12.94 | 18.33 |
| VAL | 6.01 | 15.63 | 20.42 | 26.48 | 37.10 |
| Total Concentration | 75.37 | 195.97 | 246.11 | 341.81 | 509.28 |
| Total Essential | 32.22 | 83.78 | 105.84 | 145.49 | 214.87 |
| Total Bold | 21.39 | 55.61 | 71.37 | 95.46 | 137.61 |
| Bold/Essential | 66% | 66% | 67% | 66% | 64% |
| Bold/Total | 28% | 28% | 29% | 28% | 27% |
| Essential/Total | 43% | 43% | 43% | 43% | 42% |

In Table 4, the bold amino acids are valine, threonine, leucine and lysine, the italicized amino acids are the essential amino acids (e.g., arginine, histidine, leucine, isoleucine, lysine, methionine, tryptophan, threonine, and valine; and for CHO cell cultures, proline is additionally an essential amino acid; one of skill in the art is aware of variations in the definition of essential amino acids as it applies to different cells, etc.). Table 4 provides representative desired cell culture media for CHO cells at a variety of target cell densities (M), target titers (N), cell maintenance requirements (Y), and baseline adjustments (F).

One of skill in the art will recognize that the rationally designed media of the invention may be used to either produce a polypeptide of interest, or may be used in cell culturing that is not designed for polypeptide production. Accordingly, a rationally designed media may be used in the disclosed methods of cell culturing, e.g., for the efficient growth, replication and/or maintenance of cell cultures, e.g., large-scale cell cultures, that do not contain host cells engineered to produce an exogenous polypeptide of interest, or which are not cultured to produce an endogenous polypeptide of interest. In such an instance, the desired cell culture medium need not account for the amino acid(s) required for incorporation into the polypeptide of interest, and instead contains an amino acid concentration(s) based on the concentration of the amino acid(s) required for: 1) desired cell mass, and 2) cell maintenance. Such a desired cell culture medium used in the disclosed methods of cell culturing contains a baseline-adjusted amino acid concentration, A', according to the formula A'= [(M*X)+(Y*M*X)]*F, wherein X is a concentration of the amino acid that is used per unit of cell mass, M is a multiplier for a desired peak cell mass (e.g., desired peak cell density, etc.) of the cell culture, Y is a cell maintenance factor, and F is a baseline factor. A desired cell culture medium produced according to this formula is then provided to a cell culture under conditions that allow growth and replication of the cells in the cell culture. In one embodiment of the invention, the method of cell culturing uses a large-scale cell culture. In another embodiment of the invention, the method of cell culturing uses animal cells.

Proline Addition to Cell Culture Media

Using the rational media design methods disclosed herein, it has been determined that maintaining high proline levels throughout the culture period of cell culture, e.g., large-scale cell culture, results in increased polypeptide titer and increased cell density. This proline "threshold" ranges from about 1 mM to about 2 mM, and a level of proline in the cell culture maintained above this threshold appears to be a driving force for producing high cell density, high titer large-scale cell cultures. Interestingly, the proline-driven increased polypeptide titer and cell viability concomitantly increases the culture's requirement for additional amino acids (in order to satisfy the increased consumption rate), which at least partially explains why the rationally designed media formulations herein contain high amino acid concentrations.

Providing a Cell Culture

Various methods of preparing mammalian cells for production of polypeptides by batch and fed-batch culture are well known in the art. As described above, a nucleic acid sufficient to achieve expression (typically a vector containing the nucleic acid encoding the polypeptide of interest and any operably linked genetic control elements) may be introduced into the host cell line by any number of well-known techniques. Typically, cells are screened to determine which of the host cells have actually taken up the vector and express the polypeptide or protein of interest. Traditional methods of detecting a particular polypeptide or protein of interest expressed by mammalian cells include, but are not limited to, immunohistochemistry, immunoprecipitation, flow cytometry, immunofluorescence microscopy, SDS-PAGE, Western blots, enzyme-linked immunosorbent assay (ELISA), high performance liquid chromatography (HPLC) techniques, biological activity assays and affinity chromatography. One of ordinary skill in the art will be aware of other appropriate techniques for detecting expressed polypeptides or proteins. If multiple host cells express the polypeptide or protein of interest, some or all of the listed techniques can be used to determine which of the cells expresses that polypeptide or protein at the highest levels.

Once a cell that expresses the polypeptide or protein of interest has been identified, the cell is propagated in culture by any of the variety of methods well known to one of ordinary skill in the art. The cell expressing the polypeptide or protein of interest is typically propagated by growing it at a temperature and in a medium that is conducive to the survival, growth and viability of the cell. The initial culture can be of any volume, but is often of lower volume than the culture volume of the production bioreactor used in the final production of the polypeptide or protein of interest, and frequently cells are passaged several times in bioreactors of increasing volume prior to seeding the production bioreactor. The cell culture can be agitated or shaken to increase oxygenation of the medium and dispersion of nutrients to the cells. Alternatively or additionally, special sparging devices that are well known in the art can be used to increase and control oxygenation of the culture. In accordance with the present invention, one of ordinary skill in the art will understand that it can be beneficial to control or regulate certain internal conditions of a cell culture, including but not limited to pH (e.g., 6.6 to 7.6), temperature (e.g., 25° C. to 42° C.), levels of oxygen and carbon dioxide (e.g., $O_2$: 10% to 80% and $CO_2$: 7% to 15%, throughout culture), and osmolality (e.g., a starting osmolality of 260 to 340 mOsm/kg), etc.

As used herein, the term "inoculum" is used to refer to a volume of cells containing the nucleic acid that expresses the polypeptide of interest, which is used to seed the production vessel in which the large-scale animal culture will occur, e.g., the production bioreactor. In one embodiment of the invention, the inoculum volume is about 60 to 80% of the final volume.

The starting cell density in the production bioreactor can be chosen by one of ordinary skill in the art. In accordance with the present invention, the starting cell density in the production bioreactor can be as low as a single cell per culture volume. In preferred embodiments of the present invention, starting cell densities in the production bioreactor can range from about $0.1 \times 10^6$ viable cells per mL to about $10 \times 10^6$ viable cells per mL and higher.

Initial and intermediate cell cultures may be grown to any desired density before seeding the next intermediate or final production bioreactor. In one embodiment of the invention, the inoculum cell density is about $0.5-1 \times 10^6$ cells/ml. It is preferred that most of the cells remain alive prior to seeding, although total or near total viability is not required. In one embodiment of the present invention, the cells may be removed from the supernatant, for example, by low-speed centrifugation. It may also be desirable to wash the removed cells with a medium before seeding the next bioreactor to remove any unwanted metabolic waste products or medium components. The medium may be the medium in which the cells were previously grown or it may be a different medium or a washing solution selected by the practitioner of the present invention.

The cells may then be diluted to an appropriate density for seeding the production bioreactor. The cells can be diluted into another medium or solution, e.g., the starting cell culture medium or the desired cell culture medium, depending on the needs and desires of the practitioner of the present invention or to accommodate particular requirements of the cells themselves (e.g., if the cells are to be stored for a short period of time prior to seeding the production bioreactor).

Initial Growth Phase

Once the production vessel is seeded as described above, the animal cell culture may be maintained in the initial growth phase using the desired cell culture medium obtained by the inventive formula disclosed herein, and under conditions conducive to the survival, growth and viability of the cell culture. The precise conditions will vary depending on the cell type, the organism from which the cell was derived, and the nature and character of the expressed polypeptide or protein.

A production bioreactor can be any volume that is appropriate for large-scale production of polypeptides or proteins. In a preferred embodiment, the volume of the production bioreactor is at least 500 liters. In other preferred embodiments, the volume of the production bioreactor is 1000, 2500, 5000, 8000, 10,000, 12,000 liters or more, or any intermediate volume. One of ordinary skill in the art will be aware of, and will be able to choose, a suitable bioreactor for use in practicing the present invention. The production bioreactor may be constructed of any material that is conducive to cell growth and viability that does not interfere with expression or stability of the produced polypeptide or protein.

The temperature of the cell culture in the initial growth phase will be selected based primarily on the range of temperatures at which the cell culture remains viable. For example, during the initial growth phase, CHO cells grow well at 37° C. In general, most mammalian cells grow well within a range of about 35° C. to 39° C. In one embodiment of the invention, the temperature for growth phase (day 0 to day 3) is 37° C., and the temperature for production phase (after day 3) is 31° C. Those of ordinary skill in the art will be able to select appropriate temperature or temperatures in which to grow cells, depending on the needs of the cells and the production requirements of the practitioner.

In one embodiment of the present invention, the temperature of the initial growth phase is maintained at a single, constant temperature. In another embodiment, the temperature of the initial growth phase is maintained within a range of temperatures. For example, the temperature may be steadily increased or decreased during the initial growth phase. Alternatively, the temperature may be increased or decreased by discrete amounts at various times during the initial growth phase. One of ordinary skill in the art will be able to determine whether a single or multiple temperatures should be used, and whether the temperature should be adjusted steadily or by discrete amounts.

The cells may be grown during the initial growth phase for a greater or lesser amount of time, depending on the needs of the practitioner and the requirement of the cells themselves. In one embodiment, the cells are grown for a period of time sufficient to achieve a viable cell density that is a given percentage of the maximal viable cell density that the cells would eventually reach if allowed to grow undisturbed. For example, the cells may be grown for a period of time sufficient to achieve a desired viable cell density of 1, 5, 10, 15, 20, 25, 30, 35, 40, 45, 50, 55, 60, 65, 70, 75, 80, 85, 90, 95 or 99 percent or more of maximal viable cell density.

In another embodiment the cells are allowed to grow for a defined period of time. For example, depending on the starting concentration of the cell culture, the temperature at which the cells are grown, and the intrinsic growth rate of the cells, the cells may be grown for 0, 1, 2, 3, 4, 5, 6, 7, 8, 9, 10, 11, 12, 13, 14, 15, 16, 17, 18, 19, 20 or more days. In some cases, the cells may be allowed to grow for a month or more. The cells would be grown for 0 days in the production bioreactor if their growth in a seed bioreactor, at the initial growth phase temperature, was sufficient that the viable cell density in the production bioreactor at the time of its inoculation is already at the desired percentage of the maximal viable cell density. The practitioner of the present invention will be able to choose the duration of the initial growth phase depending on polypeptide or protein production requirements and the needs of the cells themselves.

The cell culture may be agitated or shaken during the initial culture phase in order to increase oxygenation and dispersion of nutrients to the cells. In accordance with the present invention, one of ordinary skill in the art will understand that it can be beneficial to control or regulate certain internal conditions of the bioreactor during the initial growth phase, including but not limited to pH, temperature, oxygenation, etc. For example, pH can be controlled by supplying an appropriate amount of acid or base, and oxygenation can be controlled with sparging devices that are well known in the art.

Shifting Culture Conditions

At the end of the initial growth phase, a culture condition(s) may be shifted so that a second set of culture conditions is applied and a metabolic shift occurs in the culture. The accumulation of inhibitory metabolites, most notably lactate and ammonia, inhibits growth. A metabolic shift, accomplished by, e.g., a change in the temperature, pH, osmolality or chemical inductant level of the cell culture, may be characterized by, e.g., a reduction in the ratio of a specific lactate production rate to a specific glucose consumption rate. In one nonlimiting embodiment, the culture conditions are shifted by changing the temperature of the culture. In another embodiment of the invention, the temperature shift occurs on day 1-7. In another embodiment of the invention, the temperature is shifted to 29° C.-32° C. In another embodiment of the invention, the temperature shift occurs at day 3, and the temperature is shifted to 31° C. Teachings regarding temperature shift and metabolic shift may be found in the art (see, e.g., U.S. Published Patent Application No. US 2006/0121568).

Subsequent Production Phase

Once the conditions of the cell culture have been shifted as discussed above, the cell culture may be maintained for a subsequent production phase under a second set of culture conditions conducive to the survival and viability of the cell culture and appropriate for expression of the desired polypeptide or protein at adequate, e.g., commercially adequate, levels.

As discussed above, the culture may be shifted by shifting one or more of a number of culture conditions including, but not limited to, temperature, pH, osmolality, and sodium butyrate levels. In one embodiment, the temperature of the culture is shifted. According to this embodiment, during the subsequent production phase, the culture is maintained at a temperature or temperature range that is lower than the temperature or temperature range of the initial growth phase. For example, during the subsequent production phase, CHO cells express recombinant polypeptides and proteins well within a range of 25° C. to 35° C. In one embodiment of the invention, the production phase begins after day 3. In another embodiment of the invention, the production phase is carried out at 31° C. As discussed in U.S. Published Patent Application No. US 2006/0121568, multiple discrete temperature shifts may be employed to increase cell density or viability or to increase expression of the recombinant polypeptide or protein.

In accordance with the formula of the present invention, a desired cell mass (e.g., cell density) and production titer (e.g., target titer) are selected in order to establish the baseline-adjusted amino acid concentration, A, and the starting amino acid concentration, B. Thus, generally the cells are maintained in the subsequent production phase until the desired cell density or production titer, or a value(s) near the desired cell density or production titer is reached. In one embodiment, the cells are maintained in the subsequent production phase until the titer of the recombinant polypeptide or protein reaches a maximum. In other embodiments, the culture may be harvested prior to this point, depending on the production requirement of the practitioner or the needs or viability of the cells themselves. For example, the cells may be maintained for a period of time sufficient to achieve a viable cell density of 1, 5, 10, 15, 20, 25, 30, 35, 40, 45, 50, 55, 60, 65, 70, 75, 80, 85, 90, 95 or 99 percent or more of maximal viable cell density. In some cases, it may be desirable to allow the viable cell density to reach a maximum, and then allow the viable cell density to decline to some level before harvesting the culture. In an extreme example, it may be desirable to allow the viable cell density to approach or reach zero before harvesting the culture.

In another embodiment of the present invention, the cells are allowed to grow for a defined period of time during the subsequent production phase. For example, depending on the concentration of the cell culture at the start of the subsequent growth phase, the temperature at which the cells are grown, and the intrinsic growth rate of the cells, the cells may be grown for 1, 2, 3, 4, 5, 6, 7, 8, 9, 10, 11, 12, 13, 14, 15, 16, 17, 18, 19, 20 or more days. In some cases, the cells may be allowed to grow for a month or more. The practitioner of the present invention will be able to choose the duration of the subsequent production phase depending on polypeptide or protein production requirements and the needs of the cells themselves. The duration of culture will help determine the amino acid concentration required for cell maintenance, which may range in the present invention from, e.g., 0% to 150% of the amino acid concentration required for cell mass.

In certain cases, it may be beneficial or necessary to supplement the cell culture, i.e., feed the cell culture, during the subsequent production phase with nutrients or other medium components that have been depleted or metabolized by the cells. For example, it might be advantageous to supplement the cell culture with nutrients or other medium components observed to have been depleted during monitoring of the cell culture (see "Monitoring Cell Culture Conditions" section, below). Alternatively or additionally, it may be beneficial or necessary to supplement the cell culture prior to the subsequent production phase. As nonlimiting examples, it may be beneficial or necessary to supplement the cell culture with hormones and/or other growth factors, particular ions (such as sodium, chloride, calcium, magnesium, and phosphate), buffers, vitamins, nucleosides or nucleotides, trace elements (inorganic compounds usually present at very low final concentrations), lipids, amino acids, or glucose (or another energy source).

These supplementary components may all be added, i.e., fed, to the cell culture at one time, or they may be provided to the cell culture in a series of additions. In one embodiment of the present invention, the supplementary components are provided to the cell culture at multiple times in proportional amounts. In another embodiment, it may be desirable to provide only certain of the supplementary components initially, and provide the remaining components at a later time. In yet another embodiment of the present invention, the cell culture is fed continually with these supplementary components.

In accordance with the present invention, the total volume added to the cell culture should optimally be kept to a minimal amount. For example, the total volume of the feeding medium, or solution containing the supplementary components, added to the cell culture may be 1, 2, 3, 4, 5, 6, 7, 8, 9, 10, 15, 20, 25, 30, 35, 40, 45 or 50% of the volume of the cell culture prior to providing the supplementary components. Thus, the feeding medium should be concentrated in order to avoid bioreactor overflow or medium component dilution. The feeding medium is preferably provided to the main culture with the same pH, temperature, etc., but with high concentrations of nutrients relative to the starting medium. In one embodiment of the invention, the feeding medium is the feeding medium designated "Feed Medium" in column 4 of Table 2.

In one embodiment of the invention, a cell culture with a starting amino acid concentration, B, is supplemented with an additional amino acid(s) in order to achieve a baseline-adjusted amino acid concentration, A. In another embodiment of the invention, the cell culture is provided with a continuous feed from about days 3-21, or periodic feeds every 2-3 days. In another embodiment of the invention, the feeding occurs from about day 3 to about day 20 (for a 21-day culture) as bolus feeds. In another embodiment of the invention, the feeding occurs as periodic feeds about every 2-3 days. In yet another embodiment of the invention, the feeding volume is about 1% to about 40% of the total cell culture volume.

The cell culture may be agitated or shaken during the subsequent production phase in order to increase oxygenation and dispersion of nutrients to the cells. In accordance with the present invention, one of ordinary skill in the art will understand that it can be beneficial to control or regulate certain internal conditions of the bioreactor during the subsequent growth phase, including but not limited to pH, temperature, oxygenation, etc. For example, pH can be controlled by supplying an appropriate amount of acid or base, and oxygenation can be controlled with sparging devices that are well known in the art.

Monitoring Cell Culture Conditions

In certain embodiments of the present invention, the practitioner may find it beneficial or necessary to periodically monitor particular conditions of the growing cell culture. Monitoring cell culture conditions allows the practitioner to determine whether the cell culture is producing the recombinant polypeptide of interest at suboptimal levels or whether the culture is about to enter into a suboptimal production phase. In order to monitor certain cell culture conditions, it may be necessary to remove small aliquots of the culture for analysis. One of ordinary skill in the art will understand that such removal may potentially introduce contamination into the cell culture, and will take appropriate care to minimize the risk of such contamination.

As nonlimiting examples, it may be beneficial or necessary to monitor temperature, pH, cell density, cell viability, integrated viable cell density, lactate levels, ammonium levels, osmolarity, or titer of the expressed polypeptide. Numerous techniques are well known in the art that will allow one of ordinary skill in the art to measure these conditions. For example, cell density may be measured using a hemacytometer, a Coulter counter, or cell density examination (CEDEX®, Innovatis, Malvern, Pa.). Viable cell density may be determined by staining a culture sample with Trypan blue. Since only dead cells take up the Trypan blue (i.e., viable cells exclude the dye), viable cell density can be determined by counting the total number of cells, dividing the number of cells that take up the dye by the total number of cells, and taking the reciprocal. HPLC can be used to determine the levels of lactate, ammonium or the expressed polypeptide or protein. Alternatively, the level of the expressed polypeptide or protein can be determined by standard molecular biology techniques such as Coomassie staining of SDS-PAGE gels, Western blotting, Bradford assays, Lowry assays, biuret assays, and UV absorbance. It may also be beneficial or necessary to monitor the post-translational modifications of the expressed polypeptide or protein, including phosphorylation and glycosylation.

Harvesting Polypeptides Produced by Cell Culture

The polypeptide of interest that is produced by the cell culture may then be purified from the culture medium or from cell extracts for use in various applications. Soluble forms of the polypeptide can be purified from conditioned media. Membrane-bound forms of the polypeptide can be purified by preparing a total membrane fraction from the expressing cell and extracting the membranes with a nonionic detergent such as TRITON® X-100 (EMD Biosciences, San Diego, Calif.). Cytosolic or nuclear proteins may be prepared by lysing the host cells (via mechanical force, Parr-bomb, sonication, detergent, etc.), removing the cell membrane fraction by centrifugation, and retaining the supernatant.

The polypeptide can be purified using other methods known to those skilled in the art. For example, a polypeptide produced by the disclosed methods can be concentrated using a commercially available protein concentration filter, for example, an AMICON® or PELLICON® ultrafiltration unit (Millipore, Billerica, Mass.). Following the concentration step, the concentrate can be applied to a purification matrix such as a gel filtration medium. Alternatively, an anion exchange resin (e.g., a MonoQ column, Amersham Biosciences, Piscataway, N.J.) may be employed; such resin contains a matrix or substrate having pendant diethylaminoethyl (DEAE) or polyethylenimine (PEI) groups. The matrices used for purification can be acrylamide, agarose, dextran, cellulose or other types commonly employed in protein purification. Alternatively, a cation exchange step may be used for purification of proteins. Suitable cation exchangers include various insoluble matrices comprising sulfopropyl or carboxymethyl groups (e.g., S-SEPHAROSE® columns, Sigma-Aldrich, St. Louis, Mo.).

The purification of the polypeptide from culture supernatant may also include one or more column steps over affinity resins, such as concanavalin A-agarose, AF-HEPARIN650, heparin-TOYOPEARL® or Cibacron blue 3GA SEPHAROSE® (Tosoh Biosciences, San Francisco, Calif.); hydrophobic interaction chromatography columns using such resins as phenyl ether, butyl ether, or propyl ether; or immunoaffinity columns using antibodies to the labeled protein. Finally, one or more high performance liquid chromatography (HPLC) steps employing hydrophobic HPLC media, e.g., silica gel having pendant methyl or other aliphatic groups (e.g., Ni-NTA columns), can be employed to further purify the protein. Alternatively, the polypeptides may be recombinantly expressed in a form that facilitates purification. For example, the polypeptides may be expressed as a fusion with proteins such as maltose-binding protein (MBP), glutathione-S-transferase (GST), or thioredoxin (TRX). Kits for expression and purification of fusion proteins are commercially available from New England BioLabs (Beverly, Mass.), Pharmacia (Piscataway, N.J.), and Invitrogen (Carlsbad, Calif.), respectively. The proteins can also be tagged with a small epitope (e.g., His, myc or Flag tags) and subsequently identified or purified using a specific antibody to the chosen epitope. Antibodies to common epitopes are available from numerous commercial sources.

As an alternative to traditional chromatography purification modes (e.g., flow-through and bind-elute chromatography purification modes), the polypeptides produced by the methods of the present invention may be purified by operating a chromatography purification column in a weak partitioning mode, a technique in which at least one product contained in the preparation, and at least one contaminant or impurity, both bind to a chromatographic resin or medium. In the weak partitioning mode, the at least one impurity binds more tightly to the medium than the polypeptide product; and as loading (of the load fluid) continues, unbound polypeptide product selectively passes through the medium and is recovered from the column effluent. Such purification results in a high degree of impurity reduction, as well as high product recovery. Such purification can be achieved on media and resins known in the art, including but not limited to, charged ion exchange medium, hydrophobic interaction chromatography resin, immobilized metal affinity chromatography resin, and hydroxyapatite resin. In at least one embodiment, impurity/contaminant removal under weak partitioning conditions occurs as the load fluid passes through a medium/resin that binds at least 2.8 mg of product per ml of medium/resin. In at least one other embodiment, impurity/contaminant removal under weak partitioning conditions occurs as the load fluid passes through a medium/resin at operating conditions defined by a partition coefficient of at least 0.1. The purified product is recovered from the effluent of the column containing the medium/resin.

Table 5 summarizes the differences in the characteristics between flow-through (FT), bind-elute (B-E), and the weak partitioning (WP) modes.

TABLE 5

Characteristics of FT/WP/B-E Modes

| | FT | WP | B-E |
|---|---|---|---|
| $K_p$ | <0.1 | 0.1-20 | >20 |
| Load challenge limitation | Impurities 10-50 mg Prod/mL (typical) but actually dependent on load purity | Impurities 50-500 mg Prod/mL (typical) but actually dependent on load purity | Product + impurities <100 mg Prod/mL |
| Load Vol. | Moderate, for dilute impurities 10-20 CVs | Very high, for dilute impurities up to 50 CVs | Lower, as the product binds in addition to impurities 5-20 CVs |
| [Product] in load eluate | Equal to load concentration through much of load | Initial lag, then equal to load concentration through much of load | <5% of load concentration |
| Residual [Impurity] | Low | Very low | Dependent on elution conditions, pool volume and capacity |
| Product bound (Q) | <1 mg/mL | <10-20 mg/mL | >10-20 mg/mL |
| Operating region | Relatively broad range of conditions | Modest window of operation between FT and B-E modes | Stringent binding conditions for load, broad range of elution conditions |
| Mobile phase(s) | Isocratic | Isocratic | Change in buffer composition after load which causes elution |

The partition coefficient (Kp) is the ratio of the concentration of the adsorbed product (Q) to the concentration of the product in solution (C); thus the Kp for the weak partitioning mode is intermediate between the Kp for the flow-through and bind-elute modes, e.g., between about 0.1 and 20. In order to determine the proper conditions, e.g., salt, buffer, pH, etc., for a weak partitioning mode of purification, a high-throughput screen or a batch purification screening study can be performed. Thus, one skilled in the art can determine product partition coefficients Kp as a function of operating conditions (see Example 7.1).

Purification methods using a weak partitioning mode are described in detail in U.S. patent application Ser. Nos. 11/372,054 and 11/510,634, both of which are incorporated by reference herein in their entireties.

Some or all of the foregoing purification steps in various combinations or with other known methods, can be employed to purify a polypeptide of interest produced by the large-scale animal cell culture methods and media described herein.

Pharmaceutical Compositions Containing Polypeptides Produced by Cell Culture

The foregoing cell culture media, e.g., large-scale cell culture media, and methods of culturing cells provides polypeptides of interest, e.g., antibodies, soluble receptors, fusion proteins, etc. The polypeptides produced by the disclosed cell culturing methods, and with the novel media and related methods disclosed herein, including antibodies and fragments thereof, may be used in vitro, ex vivo, or incorporated into pharmaceutical compositions and administered to individuals (e.g., human subjects) in need thereof. Several pharmacogenomic approaches to consider in determining whether to administer a polypeptide of the invention are well known to one of skill in the art and include genome-wide association, candidate gene approach, and gene expression profiling. A pharmaceutical composition of the invention is formulated to be compatible with its intended route of administration (e.g., oral compositions generally include an inert diluent or an edible carrier). Other nonlimiting examples of routes of administration include parenteral (e.g., intravenous), intradermal, subcutaneous, oral (e.g., inhalation), transdermal (topical), transmucosal, and rectal administration. The pharmaceutical compositions compatible with each intended route are well known in the art.

A polypeptide of the invention may be used as a pharmaceutical composition when combined with a pharmaceutically acceptable carrier. Such a composition may contain, in addition to a polypeptide of the invention, carriers, various diluents, fillers, salts, buffers, stabilizers, solubilizers, and other materials well known in the art. The term "pharmaceutically acceptable" means a nontoxic material that does not interfere with the effectiveness of the biological activity of the active ingredient(s). The characteristics of the carrier will depend on the route of administration.

The pharmaceutical composition of the invention may also contain additional therapeutic factors or agents for treatment of the particular targeted disorder. For example, a pharmaceutical composition for treatment of type 2 diabetes may also include an oral antidiabetic agent. The pharmaceutical composition may contain thrombolytic or antithrombotic factors such as plasminogen activator and Factor VIII. The pharmaceutical composition may further contain anti-inflammatory agents. Such additional factors and/or agents may be included in the pharmaceutical composition to produce a synergistic effect with a polypeptide of the invention, or to minimize side effects caused by the polypeptides of the invention.

The pharmaceutical composition of the invention may be in the form of a liposome in which a polypeptide of the invention is combined, in addition to other pharmaceutically acceptable carriers, with amphipathic agents such as lipids that exist in aggregated form as micelles, insoluble monolayers, liquid crystals, or lamellar layers in aqueous solution. Suitable lipids for liposomal formulation include, without limitation, monoglycerides, diglycerides, sulfatides, lysolecithin, phospholipids, saponin, bile acids, etc.

As used herein, the term "therapeutically effective amount" means the total amount of each active component of the pharmaceutical composition or method that is sufficient to show a meaningful patient benefit, e.g., amelioration of symptoms of, healing of, or increase in rate of healing of such conditions. When applied to an individual active ingredient, administered alone, the term refers to that ingredient alone. When applied to a combination, the term refers to combined amounts of the active ingredients that result in the therapeutic effect, whether administered in combination, serially or simultaneously.

In practicing the method of treatment or use of the present invention, a therapeutically effective amount of a polypeptide of the invention is administered to a subject, e.g., a mammal (e.g., a human). A polypeptide of the invention may be administered in accordance with the method of the invention either alone or in combination with other therapies. When coadministered with one or more agents, a polypeptide of the invention may be administered either simultaneously with the second agent, or sequentially. If administered sequentially, the attending physician will decide on the appropriate sequence of administering the polypeptides of the invention in combination with other agents.

When a therapeutically effective amount of a polypeptide of the invention is administered orally, the binding agent will be in the form of a tablet, capsule, powder, solution or elixir. When administered in tablet form, the pharmaceutical composition of the invention may additionally contain a solid carrier such as a gelatin or an adjuvant. The tablet, capsule, and powder contain from about 5 to 95% binding agent, and preferably from about 25 to 90% binding agent. When administered in liquid form, a liquid carrier such as water, petroleum, oils of animal or plant origin, such as peanut oil (exercising caution in relation to peanut allergies), mineral oil, soybean oil, or sesame oil, or synthetic oils may be added. The liquid form of the pharmaceutical composition may further contain physiological saline solution, dextrose or other saccharide solution, or glycols such as ethylene glycol, propylene glycol, or polyethylene glycol. When administered in liquid form, the pharmaceutical composition contains from about 0.5% to about 90% by weight of the binding agent, and preferably from about 1% to about 50% by weight of the binding agent.

When a therapeutically effective amount of a polypeptide of the invention is administered by intravenous, cutaneous or subcutaneous injection, the polypeptide of the invention will be in the form of a pyrogen-free, parenterally acceptable aqueous solution. The preparation of such parenterally acceptable protein solutions, having due regard to pH, isotonicity, stability, and the like, is within the skill of those in the art. A preferred pharmaceutical composition for intravenous, cutaneous, or subcutaneous injection should contain, in addition to the polypeptide of the invention, an isotonic vehicle such as sodium chloride injection, Ringer's injection, dextrose injection, dextrose and sodium chloride injection, lactated Ringer's injection, or other vehicle as known in the art. The pharmaceutical composition of the present invention may also contain stabilizers, preservatives, buffers, antioxidants, or any other additive(s) known to those of skill in the art.

The amount of a polypeptide of the invention in the pharmaceutical composition of the present invention will depend upon the nature and severity of the condition being treated, and on the nature of prior treatments that the patient has undergone. Ultimately, the attending physician will decide the amount of a pharmaceutical composition or polypeptide of the invention with which to treat each individual patient. Initially, the attending physician will administer low doses of a pharmaceutical composition or polypeptide of the invention and observe the patient's response. Larger doses of a pharmaceutical composition or polypeptide of the invention may be administered until the optimal therapeutic effect is obtained for the patient, and at that point the dosage is not generally increased further. It is contemplated that the various pharmaceutical compositions used to treat a subject in need thereof should contain about 0.1 µg to about 100 mg of a polypeptide of the invention per kg body weight.

The duration of intravenous (i.v.) therapy using a pharmaceutical composition of the present invention will vary, depending on the severity of the disease being treated and the condition and potential idiosyncratic response of each individual patient. It is contemplated that the duration of each application of a pharmaceutical composition or a polypeptide of the present invention may be within the range of, e.g., 1-12, 6-18, or 12-24 hrs of continuous or intermittent i.v. administration. Also contemplated is subcutaneous (s.c.) therapy using a pharmaceutical composition of the present invention. These therapies can be administered daily, weekly, or, more preferably, biweekly, or monthly. Ultimately the attending physician will decide on the appropriate duration of i.v. or s.c. therapy, or therapy with a small molecule, and the timing of administration of the therapy, using the pharmaceutical composition of the present invention.

All of the references, patents, patent applications, and publications cited in this application are hereby incorporated by reference herein in their entireties.

EXAMPLES

The Examples which follow are set forth to aid in the understanding of the invention but are not intended to, and should not be construed to, limit the scope of the invention in any way. The Examples do not include detailed descriptions of conventional methods, such as recombinant DNA techniques. Such methods are well known to those of ordinary skill in the art.

Example 1

Quantifying the Amino Acid Composition of CHO Cells

To quantify the amino acid composition of antibody-expressing CHO cells and recombinant protein-expressing CHO cells, i.e., the molar percentage of each amino acid relative to the amino acid total of cell mass (biomass), the following procedure was performed. Briefly, three CHO cell lines overexpressing antibodies or recombinant protein, more specifically anti-IL-22 antibody (recombinant human anti-IL-22 antibody), Myo-029 antibody (anti-GDF8 IgG1 monoclonal antibody), and recombinant human BMP-2, were grown in a shake flask for one (BMP-2) or three (Myo-029 and anti-IL-22) days. On the final day, the cultures were harvested and the cells spun to a concentration of $10^6$ cells/mL. A $10^6$ cell-containing pellet was washed twice with 1×PBS and the pellet resuspended in 500 µL of 5 N HCl. The cell-containing suspension was heated at 100° C. for 24 hours, at which point the suspension was vacuum centrifuged. The resulting pellet was resuspended in 500 µL PBS, and amino acid analysis was performed using gas or liquid chromatography.

Acid hydrolysis determined that methionine and tryptophan both degrade during acid hydrolysis; thus, the concentrations of these amino acids in Examples 2 and 3 were based on literature values for CHO cells. In addition, it was determined that glutamine and asparagine were converted to their acidic forms, glutamic acid and aspartic acid, respectively, during hydrolysis; thus, the concentrations for these four amino acids in Examples 2 and 3 were adjusted based on the glutamine/glutamic acid and asparagine/aspartic acid ratios reported in literature. Otherwise, it was determined that these CHO cell lines possess similar amino acid compositions, and closely matched reported values for other mammalian cells (data not shown) (see Bonarius (1996) *Biotechnol. Bioeng.* 50:299-318).

Example 2

Desired Peak Cell Density of $15 \times 10^6$ Cells/ml, and Target Anti-IL-22 Antibody Titer of 9 g/L in CHO Cells (Cell Line 1) with 32% Volume Feed Using Rationally Designed Medium Example 2.1

Rationally Designed Medium

Using the formula disclosed herein, the baseline-adjusted amino acid concentration, A, of amino acids required for $15 \times 10^6$ cells/ml producing 9 g/L anti-IL-22 antibody in CHO Cell Line 1 were determined (Table 6, column 2) (cell maintenance was set at 50%, i.e., Y=0.5). The baseline-adjusted amino acid concentration, A (Table 6, column 2), of a variety of amino acids were adjusted to obtain the modified baseline-adjusted total amino acid concentrations shown in column 3 of Table 6. The following adjustments were made: levels of Asn, Asp, and Gln were set according to U.S. Published Patent Application No. US2006/0121568A1; 2) because Ala, Glu, Gly were produced by the cell cultures, their levels were adjusted to lower values; 3) the level of Cys was adjusted due to the fact that cystine is also used in the feeding medium, and the medium value of cystine is set to that in U.S. Published Patent Application No. US2006/0121568A1; 4) levels of Arg, His, Ile, Leu, Lys, Met, Phe are 20% to 100% higher than the baseline-adjusted amino acid concentration, A, due to the fact that the feed powder, which contains a set amino acid composition, was used to make the desired cell culture medium, such that an exact match was not possible. The starting medium amino acid concentration, B (Table 6, column 4), was calculated from the modified baseline-adjusted total amino acid concentrations shown in column 3 of Table 6.

TABLE 6

Desired Cell Culture Medium Formulation

| Amino Acid | Baseline-Adjusted Amino Acid Concentration (mM) (A) | Modified Baseline-Adjusted Amino Acid Concentration (mM) | Starting Amino Acid Concentration (mM) (B) |
|---|---|---|---|
| ALA | 13.67 | 2.18 | 0.20 |
| ARG | 6.68 | 12.56 | 1.94 |
| ASN | 7.42 | 27.82 | 14.56 |
| ASP | 11.86 | 6.28 | 1.70 |
| CYS | 4.97 | 0.27 | 0.40 |
| GLU | 9.23 | 2.18 | 0.20 |
| GLN | 13.11 | 2.72 | 4.00 |
| GLY | 12.94 | 4.52 | 3.63 |
| HIS | 3.93 | 5.05 | 2.15 |
| ILE | 6.23 | 10.95 | 2.54 |
| LEU | 13.13 | 17.96 | 6.87 |
| LYS | 13.01 | 15.62 | 7.91 |
| MET | 2.82 | 5.71 | 2.38 |
| PHE | 6.19 | 7.67 | 3.76 |
| PRO | 11.50 | 11.15 | 7.36 |
| SER | 21.35 | 22.34 | 10.20 |
| THR | 13.89 | 14.18 | 8.80 |
| TRP | 3.00 | 2.89 | 1.84 |
| TYR | 7.53 | 7.55 | 5.10 |
| VAL | 15.44 | 15.24 | 10.36 |
| Total | 197.91 | 194.85 | 95.91 |

Example 2.2

Cell Density and Antibody Titer in Response to Rationally Designed Medium

Cell line 1 cells (anti-IL-22-expressing CHO cells) were obtained from shake flasks containing day 3 cultures, and were inoculated at $0.7 \times 10^6$ cells/ml on day 0 into the starting cell culture medium in a 1 L bioreactor (Applikon 2 L, (Applikon Inc, Foster City, Calif.)). On day 3 (about 80 hours), temperature was shifted from 37° C. to 31° C. and Feed Medium (see column 4 of Table 2) was added at 3.75%, 4%, 4%, 9%, 2%, 1%, 1%, 1%, 3%, 2% and 1% by volume on days 3, 5, 6, 7, 10, 11, 12, 13, 14, 17, 20, respectively, to obtain the desired cell culture medium, which contains the amino acid concentration shown in Table 6, column 3. Cell cultures were maintained at pH 7.0, in a dissolved oxygen level of 30%, and with agitation at 200 rpm. Samples were taken daily to test for cell density (CEDEX® cell counting instrument (Innovatis, Malvern, Pa.)), viability (CEDEX®) and certain metabolite levels (Nova BioProfile Analyzer, Nova Biomedical Cooperation, Waltham, Mass.). Spun-down media were saved at −80° C. for antibody titer analysis using Protein A HPLC.

Figure 2:
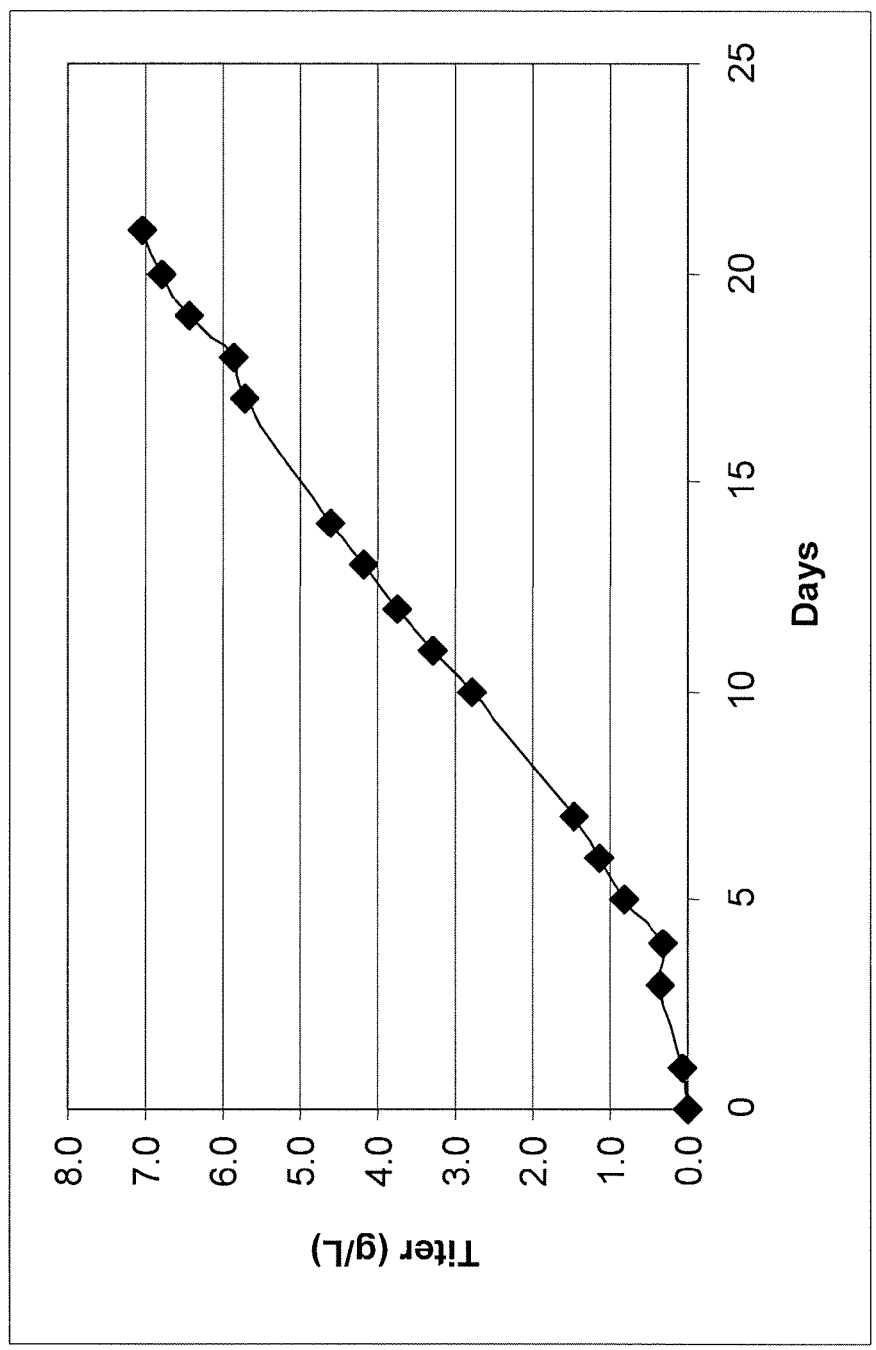
FIG. 2 depicts the titer (Y-axis; "Titer (g/L)") of anti-IL-22 antibody over time (X-axis; "Days") for CHO cells engineered to express anti-IL-22. Cells were cultured in the rationally designed medium of Example 2.

The results are shown in FIGS. 1 and 2. As can be seen from FIG. 1, the highest cell density (about $11 \times 10^6$ cells/mL) was achieved on day 11 of culture, with cell density decreasing thereafter. The highest antibody titer (about 7 g/L) was obtained on day 21 of culture. Thus, the rationally designed medium may be used to produce high cell density and high antibody titer.

Example 3

Desired Peak Density of $15 \times 10^6$ Cells/ml, and Target Anti-IL-22 Antibody Titer of 10 g/L in CHO Cells (Cell Line 2) with 33% Volume Feed Using Rationally Designed Medium

Example 3.1

Rationally Designed Medium

Using the formula disclosed herein, the baseline-adjusted amino acid concentration, A, of amino acids required for $15 \times 10^6$ cells/ml and 10 g/L anti-IL-22 antibody (described above) were determined (cell maintenance was set at 50%, i.e., Y=0.5). The baseline-adjusted amino acid concentration, A (Table 7, column 2) of a variety of amino acids were adjusted as described in Example 2 to obtain the modified baseline-adjusted total amino acid concentrations shown in column 3 of Table 7. In addition, for this medium formulation both the starting cell culture medium and the feed medium were prepared from existing powders with fixed compositions, and thus an exact match was not possible. The starting medium amino acid concentration, B (Table 7, column 4), was calculated from the modified baseline-adjusted total amino acid concentrations shown in column 3 of Table 7.

TABLE 7

Desired Cell Culture Medium Formulation

| Amino Acid | Baseline-Adjusted Amino Acid Concentration (mM) (A) | Modified Baseline-Adjusted Amino Acid Concentration (mM) | Starting Amino Acid Concentration (mM) (B) |
|---|---|---|---|
| ALA | 14.2 | 2.4 | 0.4 |
| ARG | 6.9 | 15.2 | 5.3 |
| ASN | 7.8 | 32.6 | 21.1 |
| ASP | 12.2 | 6.8 | 2.3 |
| CYS | 5.2 | 0.3 | 0.4 |
| GLU | 9.7 | 2.4 | 0.4 |
| GLN | 13.6 | 2.7 | 4.0 |
| GLY | 13.6 | 4.5 | 3.6 |
| HIS | 4.1 | 5.5 | 2.7 |
| ILE | 6.4 | 13.2 | 5.4 |
| LEU | 13.8 | 20.0 | 9.4 |
| LYS | 13.7 | 16.5 | 8.9 |
| MET | 2.9 | 6.3 | 3.1 |
| PHE | 6.5 | 8.3 | 4.5 |
| PRO | 12.3 | 12.5 | 9.1 |
| SER | 22.6 | 23.8 | 11.8 |
| THR | 14.8 | 15.7 | 10.8 |
| TRP | 3.2 | 3.2 | 2.3 |
| TYR | 8.0 | 7.6 | 5.1 |
| VAL | 16.4 | 15.4 | 10.3 |
| Total | 207.93 | 214.8 | 121.1 |

Example 3.2

Cell Density and Antibody Titer in Response to Rationally Designed Medium

Cell line 2 cells (anti-IL-22-expressing CHO cells) were obtained from shake flasks containing day 3 cultures, and the cells were inoculated at $0.7 \times 10^6$ cells/ml on day 0 into the starting cell culture medium in a 1 L bioreactor (Applikon 2 L). On day 3 (about 80 hours), temperature was shifted from 37° C. to 31° C. and feed was added continuously (1.8% by volume per day) with an automatic feeding pump, to obtain the desired cell culture medium, which contains the amino acid concentration shown in Table 7, column 3. Cell cultures were maintained at pH 7.0, in a dissolved oxygen level of 30%, and with agitation at 200 rpm. Samples were taken daily to test for cell density (CEDEX® cell counting instrument), viability (CEDEX®) and certain metabolites levels (Nova Enzymatic analyzer). Spun-down media were saved at −80° C. for antibody titer analysis using Protein A HPLC.

Figure 3:
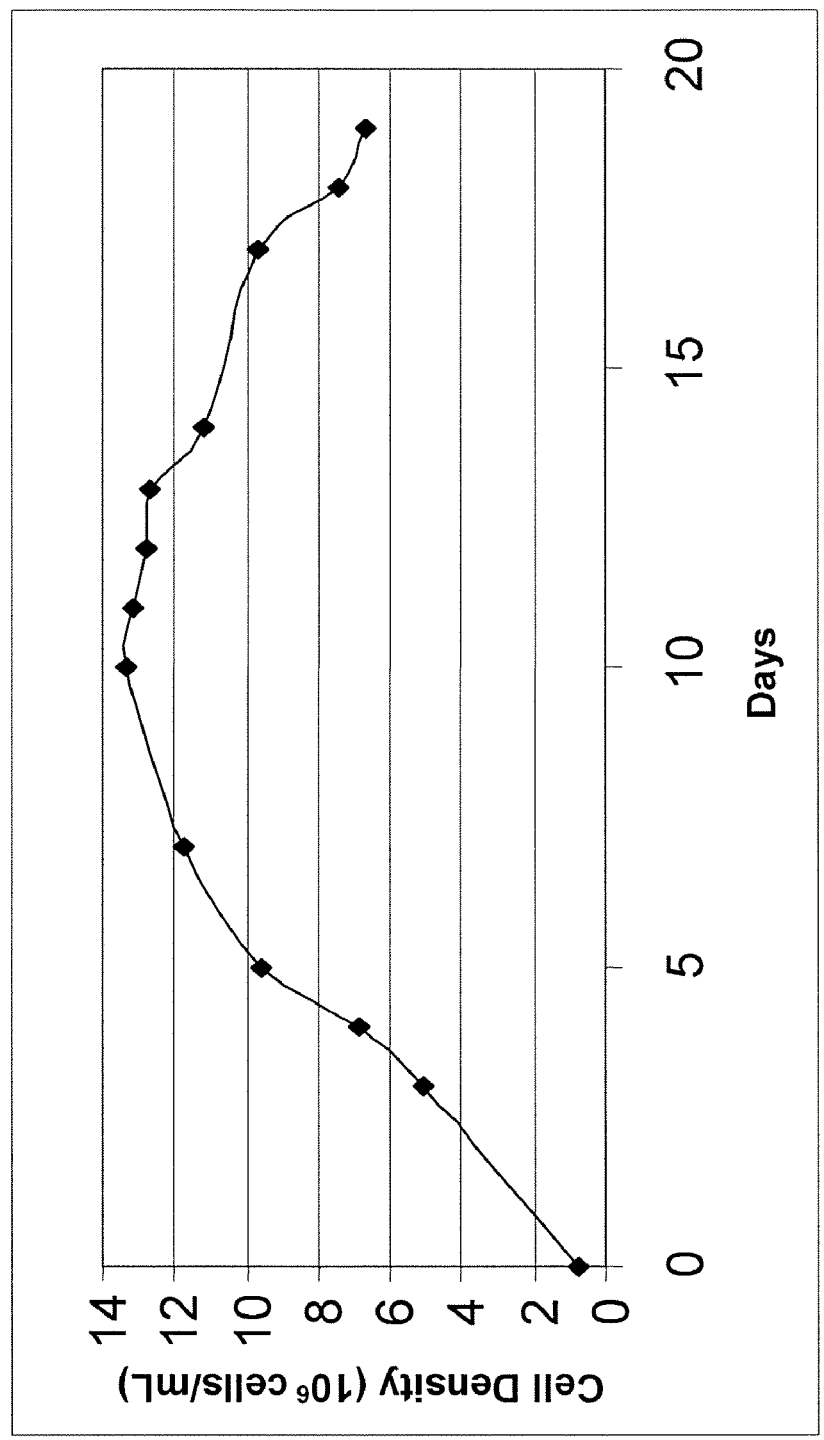
FIG. 3 depicts the cell density (Y-axis; "Cell Density ($10^6$ cells/mL)") over time (X-axis; "Days") for CHO cells engineered to express anti-IL-22. Cells were cultured in the rationally designed medium of Example 3.
Figure 4:
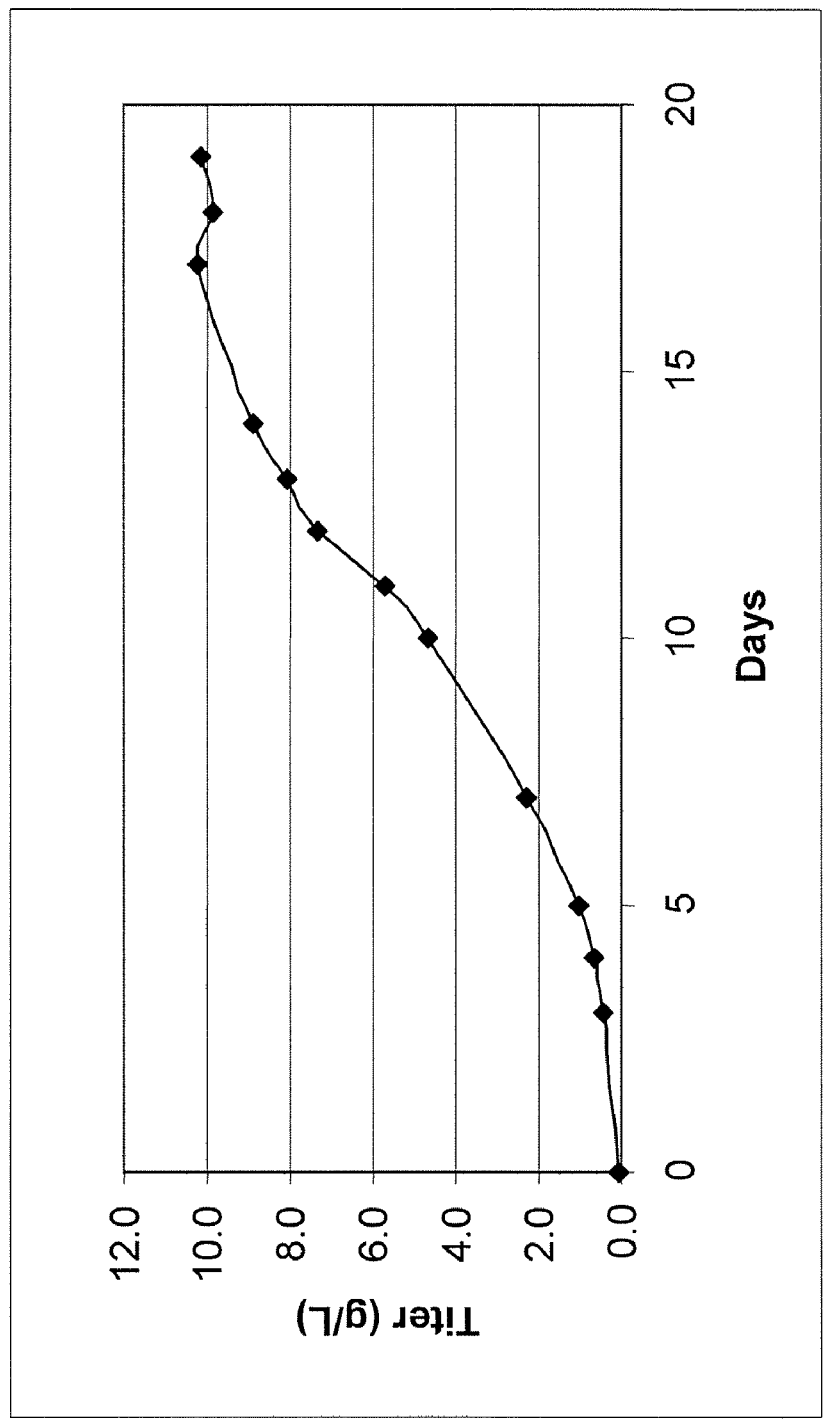
FIG. 4 depicts the titer (Y-axis; "Titer (g/L)") of anti-IL-22 antibody over time (X-axis; "Days") for CHO cells engineered to express anti-IL-22. Cells were cultured in the rationally designed medium of Example 3.

The results are shown in FIGS. 3 and 4. As can be seen from FIG. 3, the highest cell density (over $12 \times 10^6$ cells/mL) was achieved on day 10 of culture, with cell density decreasing thereafter. The highest antibody titer (over 10 g/L) was obtained on day 19 of culture. Thus, the rationally designed medium may be used to produce high cell density and high antibody titer.

Example 4

The Effect of Proline Addition on Cell Culture Performance

CHO cells producing the antibody Anti-IL-22 were cultured in pH-controlled shake flasks (500 mL flasks with 100 mL working volume), and maintained on a shaker at 100 rpm in a temperature-controlled, 7% $CO_2$ incubator. Cells were seeded at $0.7 \times 10^6$ cells/mL. The culture duration was 18 days. The first 3 days cells were maintained at 37° C., after which the temperature was shifted to 31° C. for the remainder of the culture. pH was controlled for the first 3 days with 1 M sodium bicarbonate. Cell culture medium consisted of a medium based on traditional cell culture requirements, termed "Traditional Medium," and rationally designed medium, i.e., medium formulated using the rational design disclosed herein, termed "Rational Design Medium," to achieve $10 \times 10^6$ cells/mL and 10 g/L antibody. A major difference of note between these two formulations is that several amino acids (PRO, THR, GLY, TYR, TRP, VAL, and PHE) are at higher concentrations in the "Rational Design Medium" compared to the "Traditional Medium." A third condition presented is the traditional medium with an additional 3.7 mM proline added to obtain the level of proline in the "Rational Design Medium", termed "Traditional Medium+Proline." These formulations are presented in Table 8, below. Wyeth in-house feed medium ("Feed Medium," see Table 2) was added to the culture at 23% total by volume, comprising daily feeds of 2% on days 3-4, 9-14, 17, 1% on days 5-6, and 3% on day 7.

TABLE 8

Media Formulations for Proline Studies

| 1<br>Amino<br>Acid | 2<br>Traditional<br>Medium<br>[mM] | 3<br>Rational<br>Design<br>Medium<br>[mM] | 4<br>Traditional<br>Medium +<br>Proline<br>[mM] |
|---|---|---|---|
| alanine | 0.44 | 0.44 | 0.44 |
| arginine•HCl | 5.32 | 5.32 | 5.32 |
| asparagine•$H_2O$ | 21.08 | 21.08 | 21.08 |
| aspartic acid | 2.25 | 2.25 | 2.25 |
| glutamine | 4.00 | 4.00 | 4.00 |
| glutamate | 0.24 | 0.24 | 0.24 |
| glycine | 1.78 | 3.59 | 1.78 |
| histidine | 2.68 | 2.68 | 2.68 |
| isoleucine | 5.44 | 5.44 | 5.44 |
| leucine | 9.43 | 9.43 | 9.43 |
| lysine•HCl | 8.90 | 8.90 | 8.90 |
| methionine | 3.08 | 3.08 | 3.08 |
| phenylalanine | 3.67 | 4.48 | 3.67 |
| proline | 5.41 | 9.13 | 9.13 |
| serine | 11.82 | 11.82 | 11.82 |
| threonine | 5.71 | 10.85 | 5.71 |
| tryptophan | 1.54 | 2.32 | 1.54 |
| tyrosine•2Na | 3.34 | 5.13 | 3.34 |
| valine | 7.36 | 10.30 | 7.36 |

Figure 5:
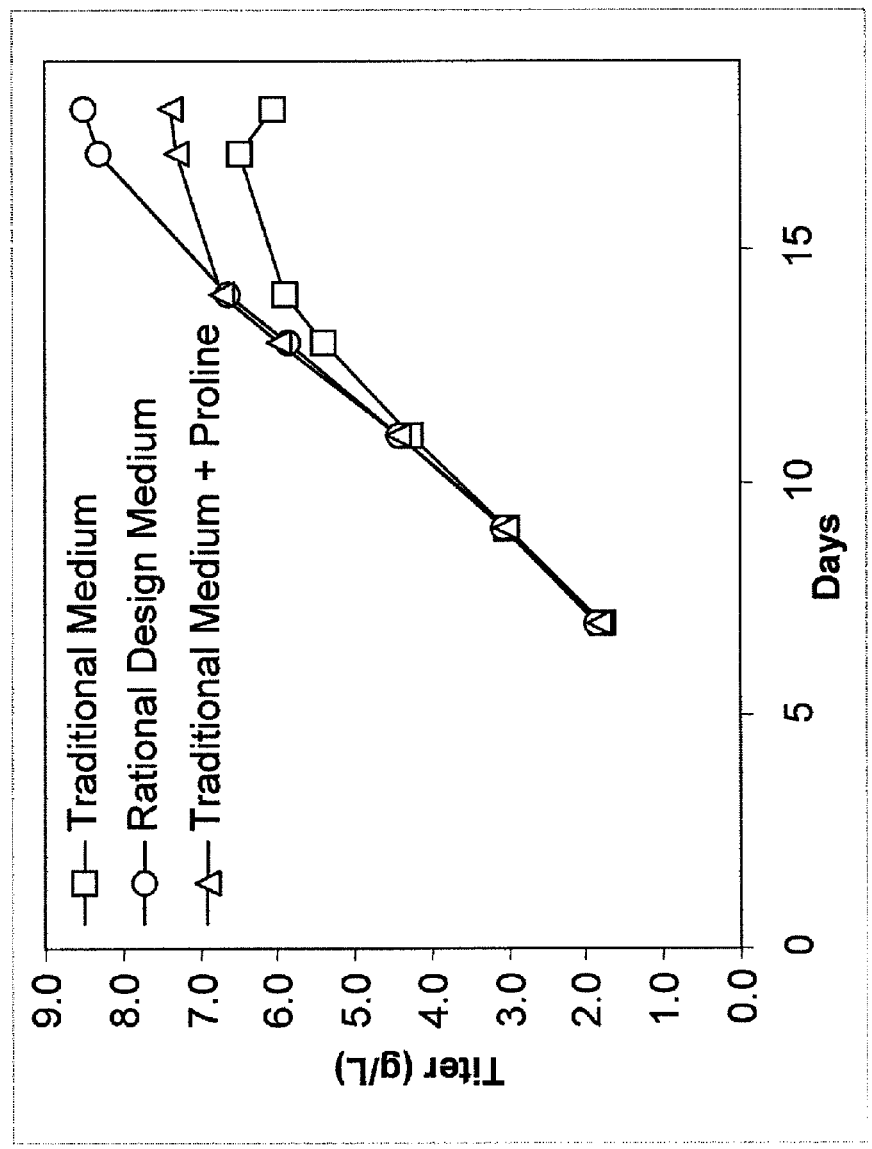
FIG. 5 depicts the titer (Y-axis; "Titer (g/L)") of anti-IL-22 antibody over time (X-axis; "Days") for CHO cells engineered to express anti-IL-22. Cells were cultured in "Traditional Medium" (a medium based on traditional cell culture requirements, see, e.g., U.S. Published Patent Application No. 2006/0121568), "Rational Design Medium" prepared using the methods herein, or "Traditional Medium+Proline," which contains an additional 3.7 mM proline added to the "Traditional Medium" (see Example 4).
Figure 6:
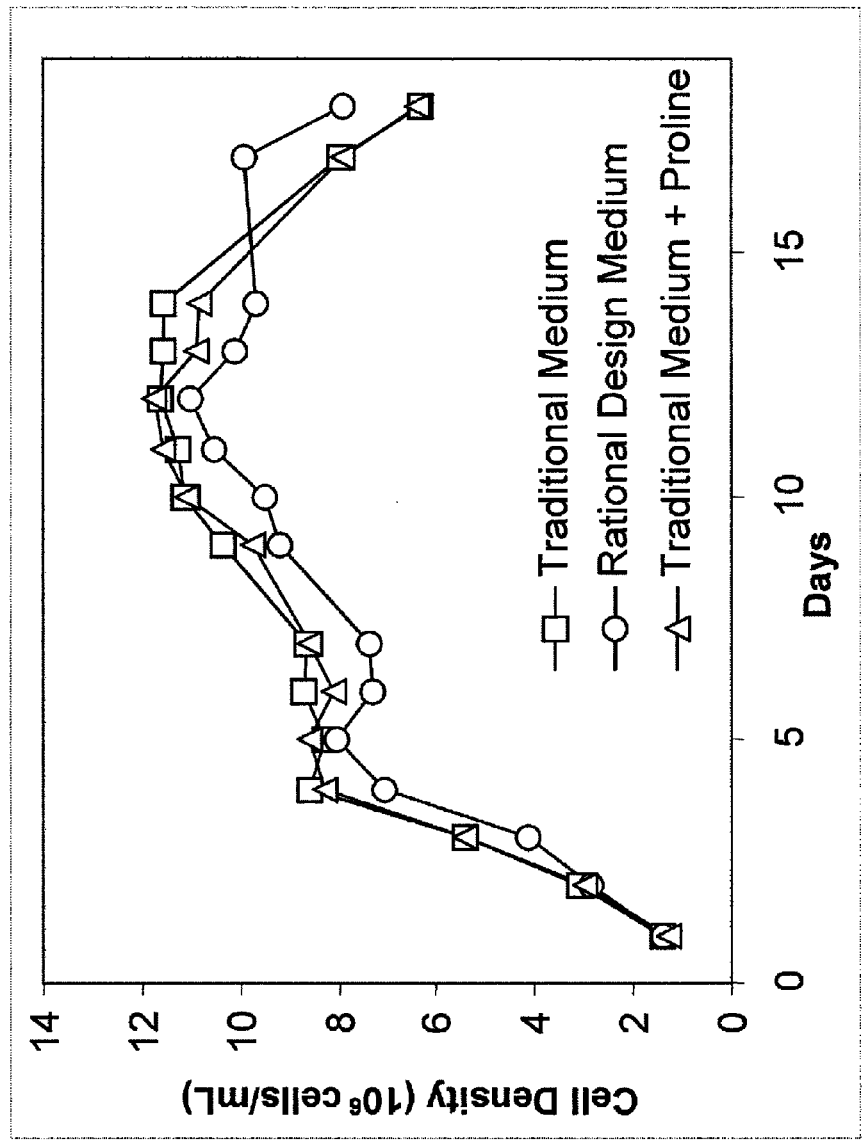
FIG. 6 depicts the cell density (Y-axis; "Cell Density ($10^6$ cells/mL)" over time (X-axis; "Days") for CHO cells engineered to express anti-IL-22. Cells were cultured in "Traditional Medium," "Rational Design Medium," or "Traditional Medium+Proline" (see Example 4).
Figure 7:
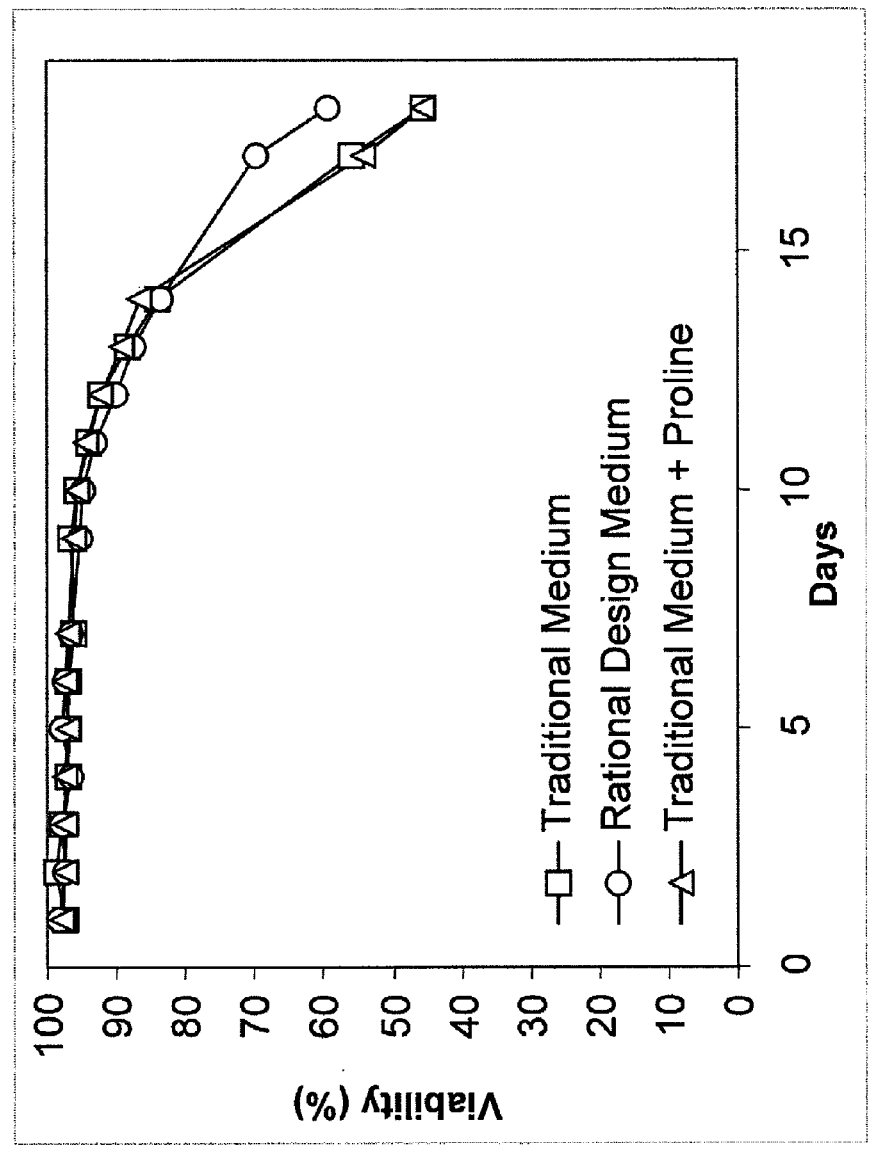
FIG. 7 depicts the cell viability (Y-axis; "Viability [%]") over time (X-axis; "Days") for CHO cells engineered to express anti-IL-22. Cells were cultured in "Traditional Medium," "Rational Design Medium," or "Traditional Medium+Proline" (see Example 4).
Figure 8A:
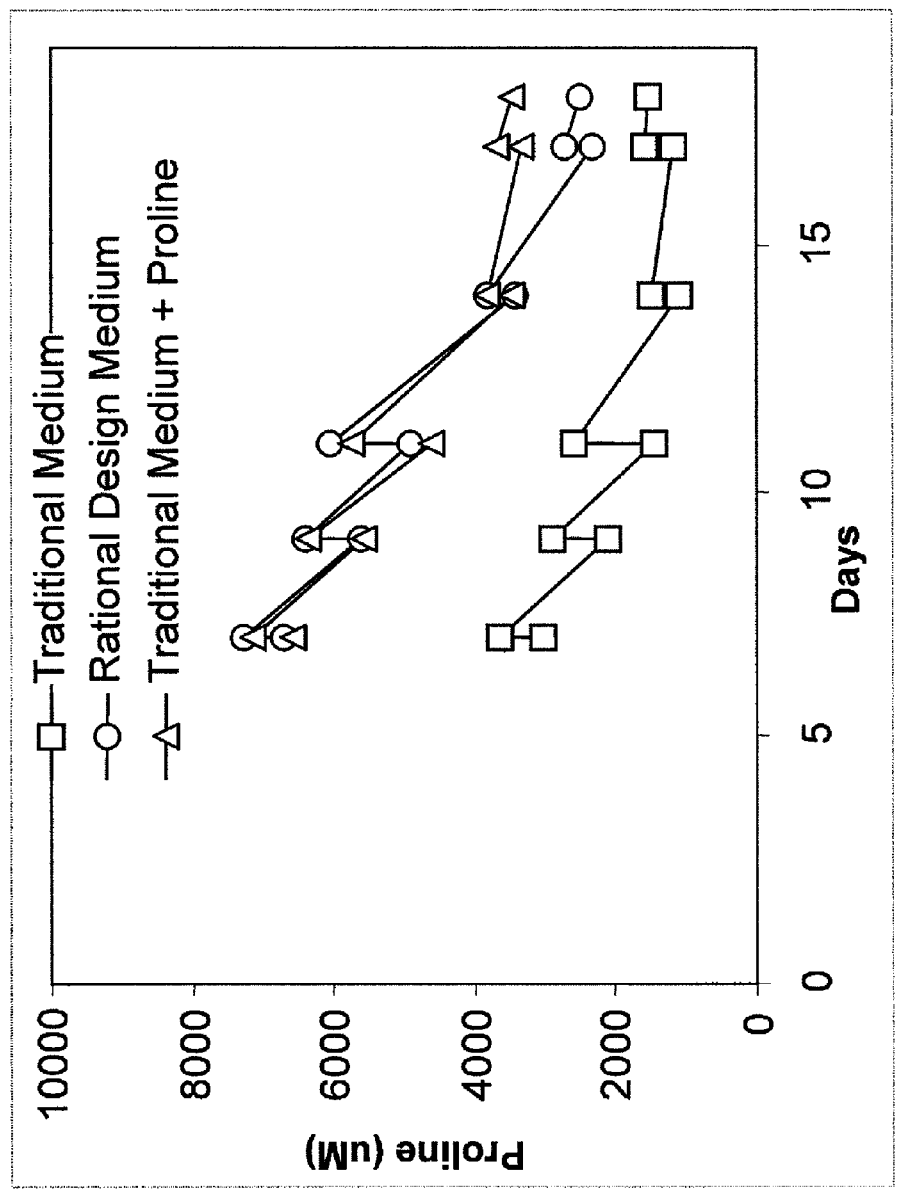
FIG. 8 depicts the concentration of the designated amino acid (Y-axis; "[µM]") ((FIG. 8A) proline.
(FIG. 8B) threonine.
(FIG. 8C) valine.
(FIG. 8D) tryptophan.
(FIG. 8E) tyrosine) over time (X-axis; "Days") for CHO cells for cells engineered to express anti-IL-22. Cells were cultured in "Traditional Medium," "Rational Design Medium," or "Traditional Medium+Proline" (see Example 4).
Figure 8C:
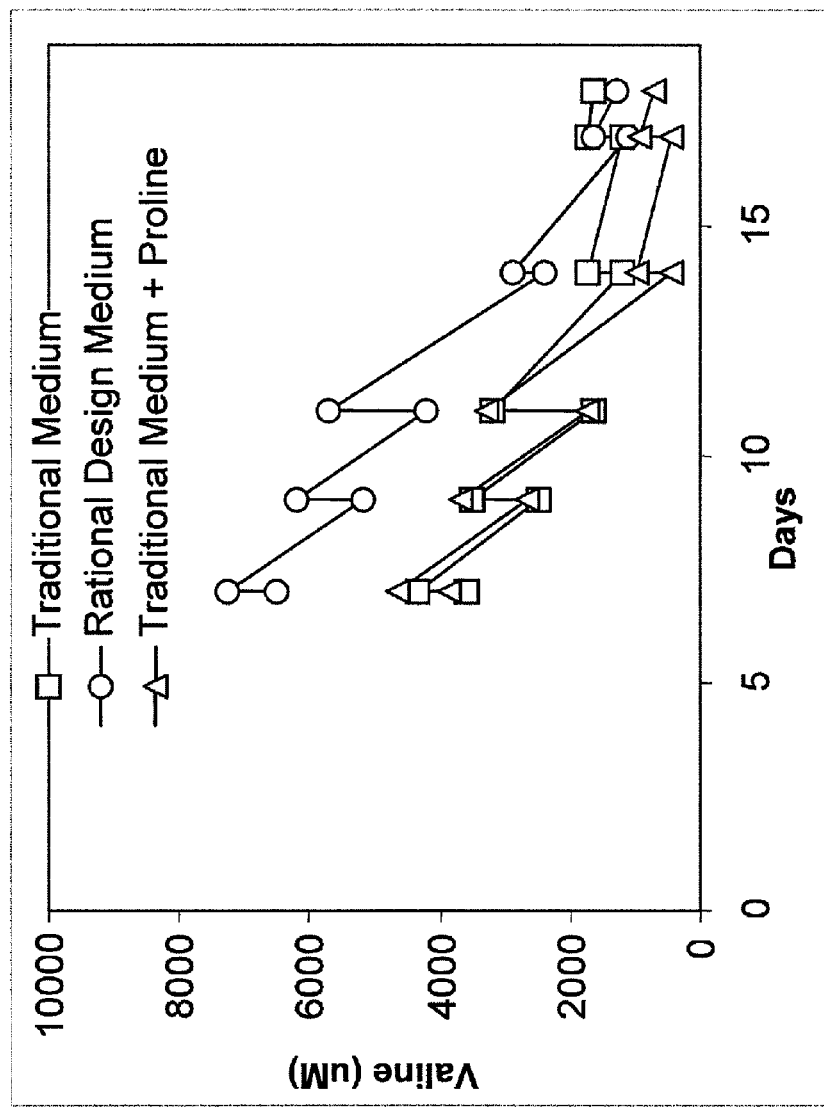
Figure 8D:
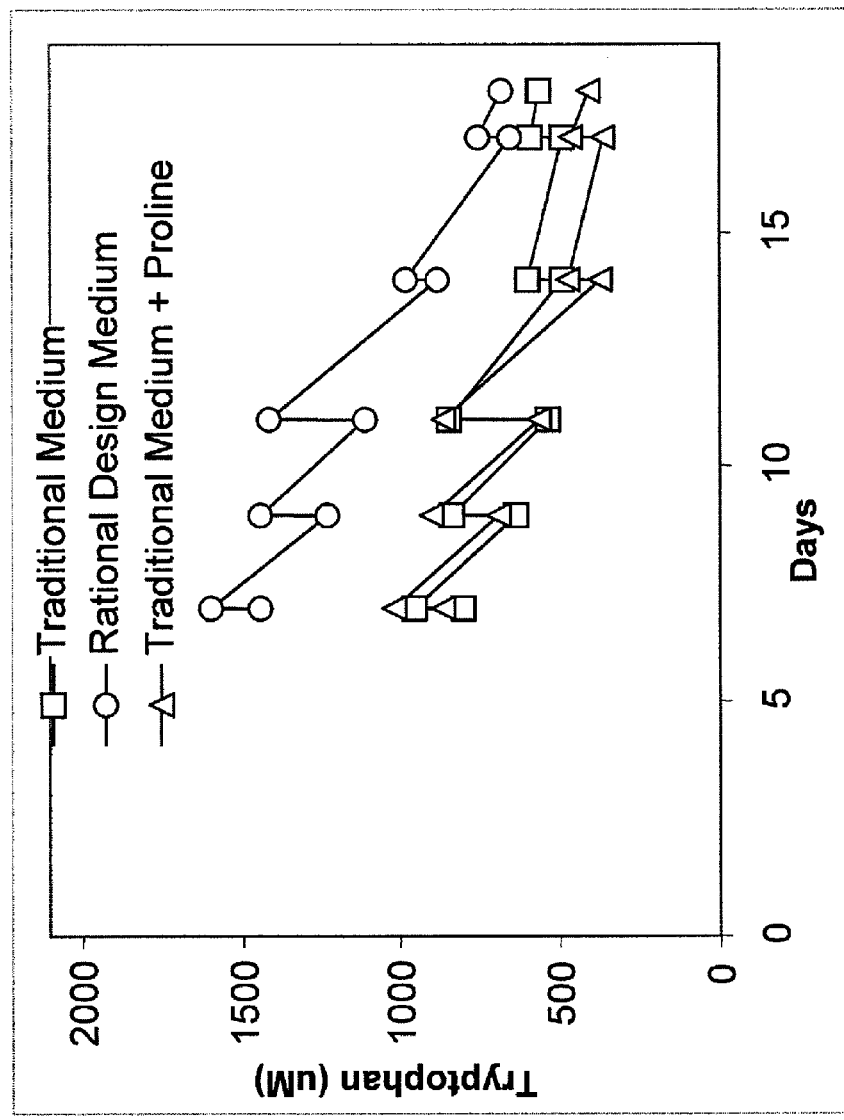
Figure 8E:
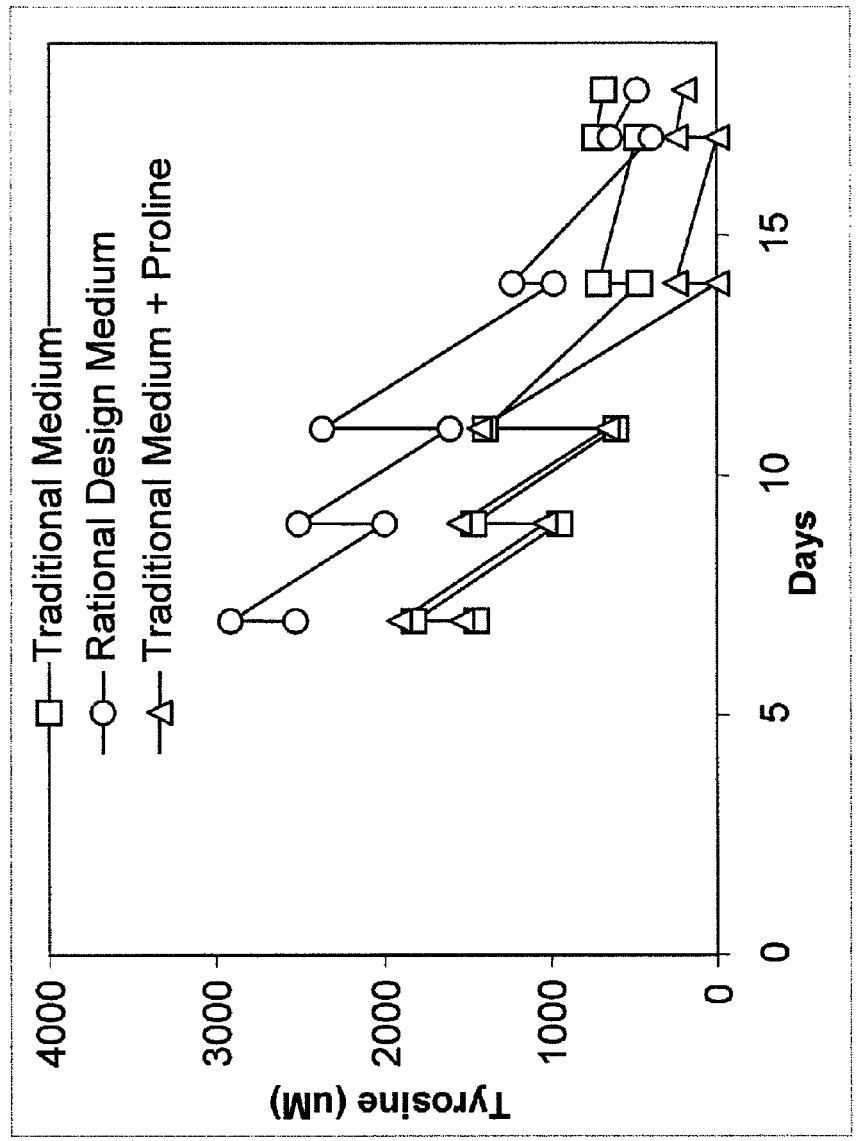

The results from these experiments are shown in FIGS. 5-7. Addition of proline to the traditional medium, i.e. "Traditional Medium+Proline" (FIG. 5), resulted in an antibody production equivalent to the "Rational Design Medium" through day 14. As shown in FIG. 6, all three media maintained a high cell density, with the highest density displayed at day 12. As shown in FIG. 7, all three media maintained high cell viability, with the "Rational Design Medium" cultures maintaining greater viability on days 15-18 in comparison to the cultures containing "Traditional Medium" and "Traditional Medium+Proline" media. As a variety of other media, which each contained one rationally designed concentration of either glycine, phenylalanine, threonine, tryptophan, tyrosine or valine did not result in cell cultures producing a higher antibody titer than the "Traditional Medium" (data not shown), proline serves as the rate-limiting amino acid required to achieve high titer. This is exemplified in FIGS. 8A-E, which show that by day 14 many of the amino acids in the "Traditional Medium+Proline" reached extremely low levels (note tyrosine was depleted), thereby preventing further incorporation of these amino acids into antibody. This result is also observed in the titer graph (FIG. 5), as the slope for the "Traditional Medium+Proline" is reduced after day 14, while antibody production is maintained through day 18 for the "Rational Design Medium," which contains higher levels of other amino acids.

Interestingly, the proline concentration in the "Traditional Medium" never dropped below 1 mM (FIG. 8A); however, the effect of proline on overall amino acid incorporation into antibody was reduced after day 11. This finding suggests that a proline threshold exists, i.e., the concentration of proline must be maintained above 1 mM throughout the culture.

Example 5

Prophetic Example

Optimized Cell Culture Media for a Novel Cell Line

The methods of media design disclosed herein may be used for any cell culture, including cell cultures that use novel cells/cell lines. The optimized media for use with a novel cell line would contain at least one baseline-adjusted amino acid concentration, A, of an amino acid according to the formula $A = [(M^*X) + (N^*P) + (Y^*M^*X)]^*F$.

A multiplier, M, when applying the above equation to a novel cell culture, may be selected, e.g., from 1 to $20 \times 10^6$ cells/mL. One of skill in the art would be able to calculate a useful M value by doubling the maximum cell density during the growth phase, which can be calculated based on the growth rate.

A multiplier, N, when applying the above equation to a novel cell culture, may be calculated, e.g., by multiplying the IVC by the cell qp. One of skill in the art would be able to calculate the IVC by estimating the growth profile, following the methods described in the section entitled "Rational Media Design and Formulations." One of skill in the art would be able to calculate the qp by measuring the antibody or recombinant protein production on a per cell basis.

A cell maintenance factor, Y, when applying the above equation to a novel cell culture, may be estimated by using Y=1 (i.e., 100% of the amino acid(s) required for desired cell mass) initially, and then refining the value of Y (higher or lower).

A baseline factor, F, when applying the above equation to a novel cell culture, may be estimated by using F=1.3 (i.e., 30% additional amino acid(s)) initially, and then refining the value of F (higher or lower).

Example 6

Effect of Maintenance and Baseline Factors on Cell Culture Performance

To demonstrate that the maintenance factor, Y, and the baseline factor, F, are important/essential for cell culture performance, anti-IL-22-expressing CHO cells were seeded at $0.7 \times 10^6$ cells/mL and cultured for 21 days in 2 L bioreactors with a pH set point of 7.0 and a dissolved oxygen (DO) setpoint of 30%. The pH was controlled by 2N $Na_2CO_3$/$NaHCO_3$, and DO was controlled by air (containing 7% $CO_2$) sparge. The temperature of the culture was 37° C. for the first 3 days and shifted to 31° C. after day 3, and remained at 31° C. until the end of the culture. Cells were cultured for 21 days in either (1) media containing amino acids required for both target protein titer and desired peak cell density (but not accounting for the maintenance factor or baseline factor), i.e., "Rational Design Medium without maintenance and baseline factors," or (2) "Rational Design Medium."

Figure 9:
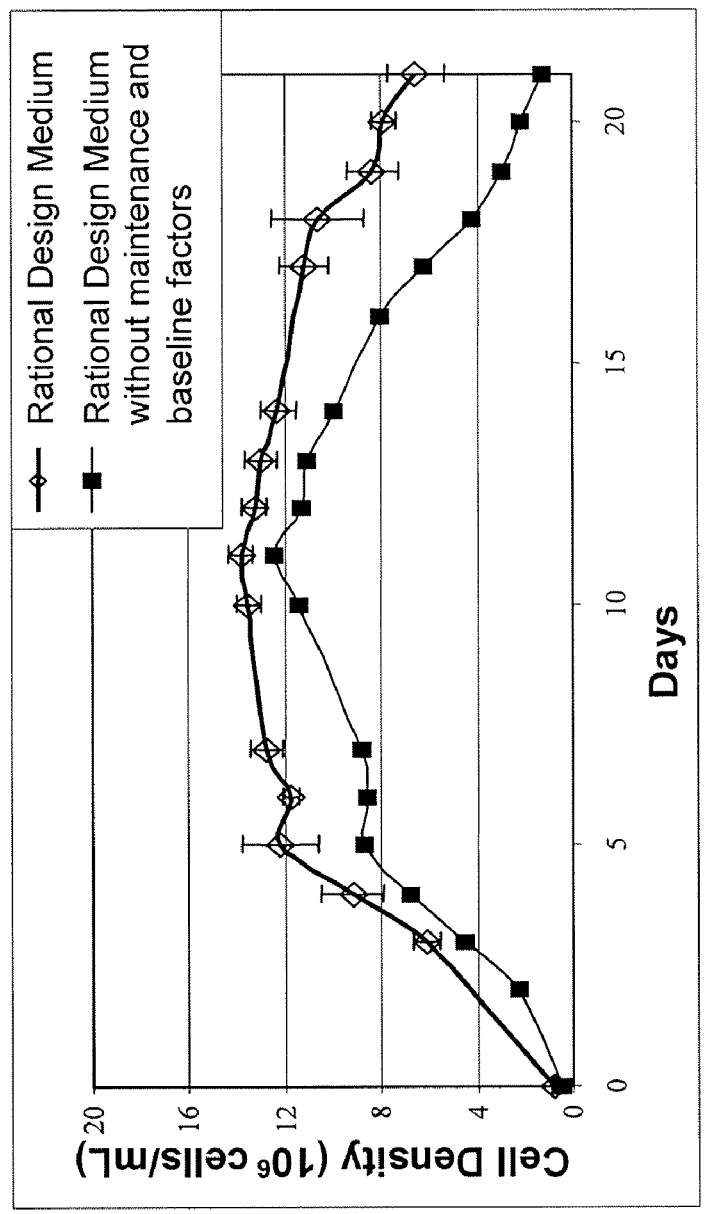
FIG. 9 depicts the cell density (Y-axis; "Cell Density ($10^6$ cells/mL)") over time (X-axis; "Days") for CHO cells engineered to express anti-IL-22. Cells were cultured in "Rational Design Medium" or "Rational Design Medium without maintenance and baseline factors." The figure is representative of 5 independent replicates (n=5) (see Example 6).
Figure 10:
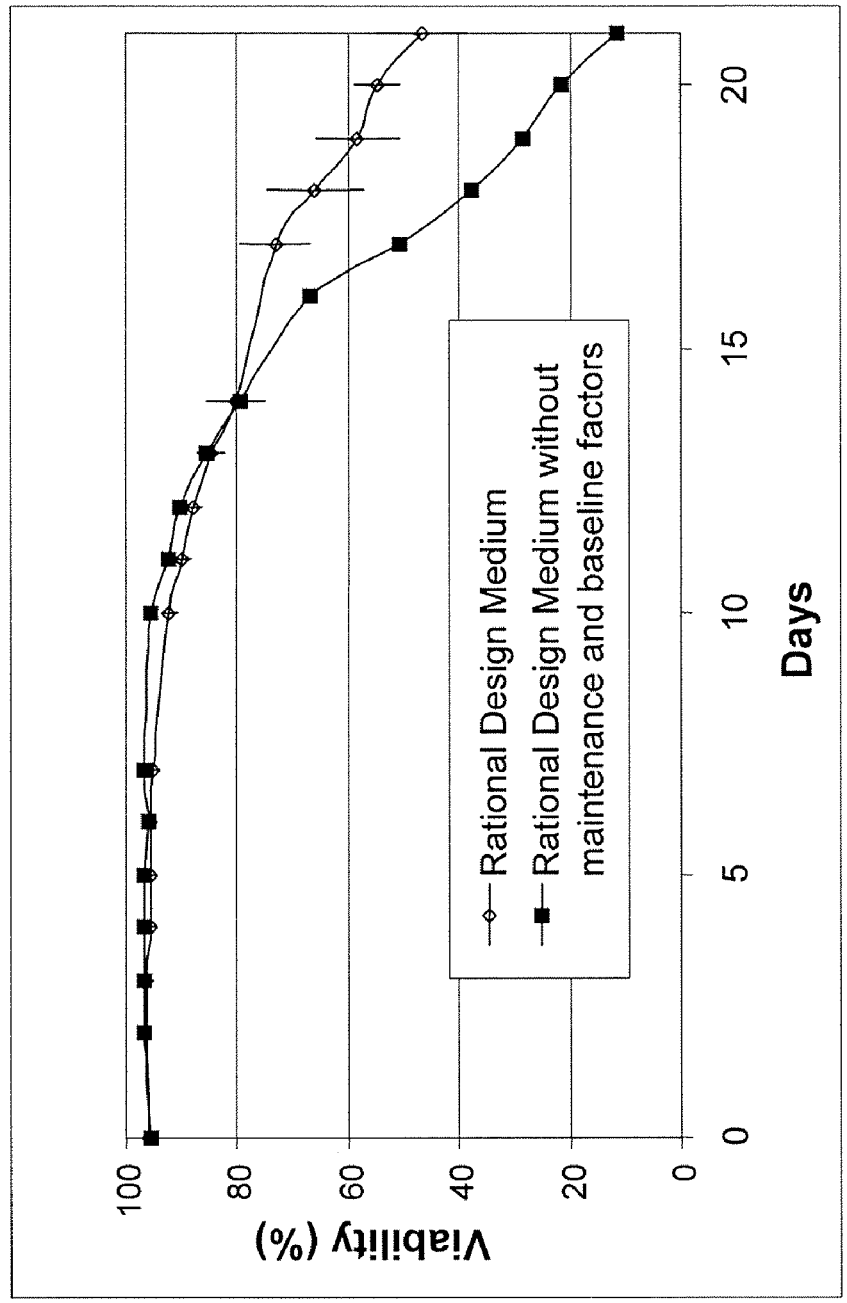
FIG. 10 depicts cell viability (Y-axis: "Viability (%)") over time (X-axis; "Days") for CHO cells engineered to express anti-IL-22. Cells were cultured in "Rational Design Medium" or "Rational Design Medium without maintenance and baseline factors." The figure is representative of 5 independent replicates (n=5) (see Example 6).

As exemplified in FIGS. 9 and 10, the medium that does not account for maintenance and baseline factors displayed a significant decrease in viability, nearly approaching 0% at day 21 of the cell culture, and a significant decrease in cell density. Moreover, FIG. 11 demonstrates that at day 21 of the cell culture, this same medium was only able to support an antibody titer of 5 g/L.

Figure 11:
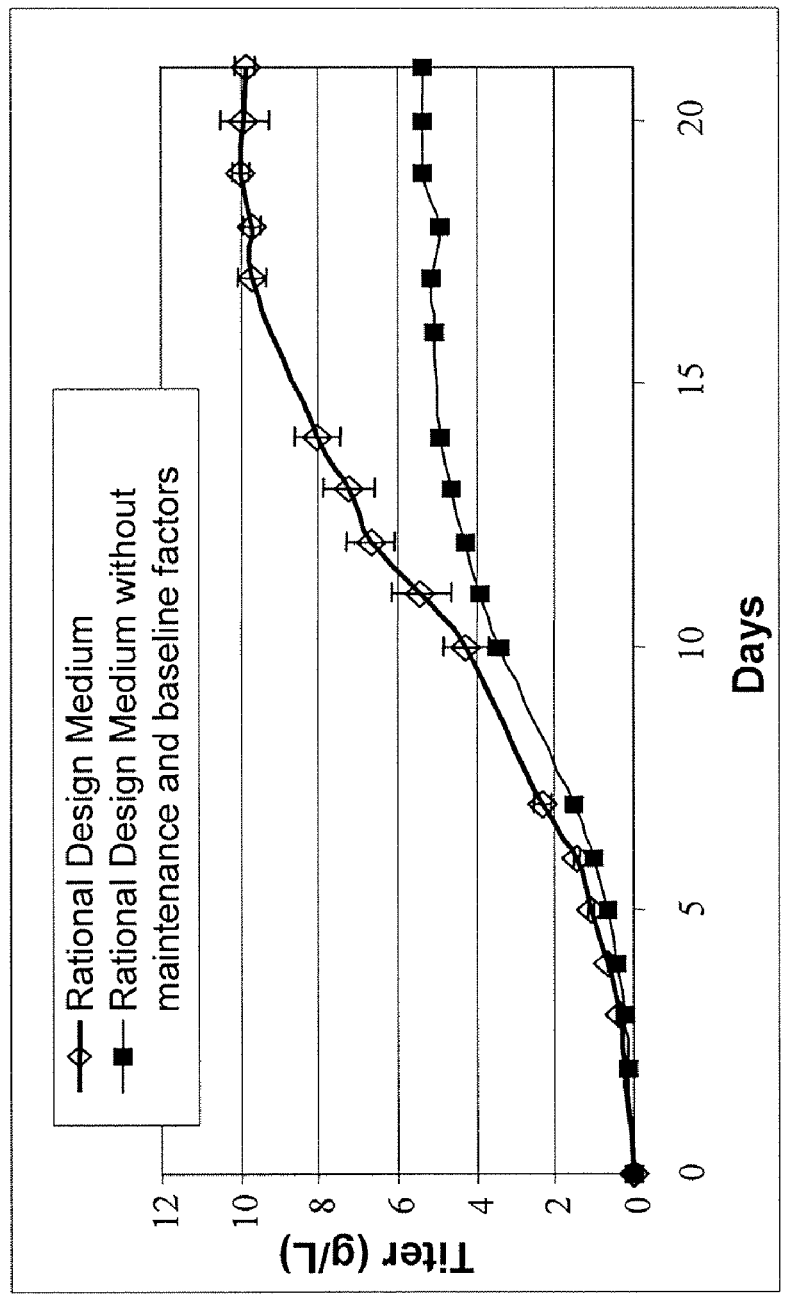
FIG. 11 depicts antibody titer (Y-axis; "Titer (g/L)") over time (X-axis; "Days") for CHO cells engineered to express anti-IL-22. Cells were cultured in "Rational Design Medium" or "Rational Design Medium without maintenance and baseline factors." The figure is representative of 5 independent replicates (n=5) (see Example 6).

In contrast, Rational Design Medium (including maintenance and baseline factors) displayed higher viability, cell density and antibody titers (FIGS. 9-11). At day 21 of the cell culture, the Rational Design Medium was able to support an antibody titer of 10 g/L.

These findings suggest that accounting for maintenance and baseline factors in determination of the amino acid concentration in the desired cell culture medium improves cell performance as measured by cell viability, cell density, and polypeptide titer.

Example 7

Polypeptide Purification Using Anion Exchange Chromatography in a Weak Partitioning Mode

Example 7.1

High-Throughput Screen to Establish Weak Partitioning and Flow-Through Conditions An initial screening study was performed first, which determined the partition coefficient and/or the concentration of product bound to the resin under various solution conditions, thus defining the operating regions of weak partitioning (WP) and flow-through (FT) modes for Mab-AAB, the polypeptide of interest, and TMAE-HiCap (M) Medium. This screen varied the concentration of sodium chloride and pH to determine their effects on the extent of binding of Mab-AAB and process-related impurities (Protein A and HCP) to the TMAE medium.

The levels of Protein A residuals in the test samples were measured using a Protein A enzyme-linked immunosorbent assay (ELISA). The amount of high molecular weight aggregate was measured using an analytical size exclusion chromatography (SEC) assay. The levels of host cell proteins (HCPs) were measured using a HCP ELISA. All screening and column studies were conducted at room temperature.

Fifty μL of TMAE HiCap medium was added to each well of a 96-well filter plate. Each well was equilibrated in solutions made up 50 mM glycine and a variable amount of Tris buffer (depending upon the amount needed for neutralization to the pH specified in Table 9) and sodium chloride (specified in Table 10). The pH ranged from 7.6 to 9.0, and the sodium chloride ranged from 0 mM to 80 mM.

The buffer solutions used in each row were diluted on an automated pipetting system (Tecan 100 RST). The stock solution for the buffers was made from 500 mM glycine acidified with HCl to pH 3.0, and subsequently neutralized with 2 M Tris Base to the pH levels indicated in Table 9. This titration resulted in a level of Tris that depended upon the pH of the buffer. The buffer pH was measured at a 1 to 10 dilution of the stock buffer concentration, which corresponded to the dilution made by the automated pipetting system. As a result of the glycine acidification to pH 3.0, the buffer contributes about 10 mM of ionic strength to the final solution. Two load (load fluid) challenges were made to the resin: 5 mg/mL to measure the partition coefficient, Kp, and 122 mg/mL to measure the capacity of the resin for removal of impurities and the bound product, Q, in equilibrium with a protein solution at a concentration approximately equal to the column load concentration.

TABLE 9

| Buffer type and pH Target in Each Well |
| --- |
| All columns |

| | |
| --- | --- |
| A | 50 mM Glycine, 8.8 mM Tris, pH 7.6 |
| B | 50 mM Glycine, 13.6 mM Tris, pH 7.8 |
| C | 50 mM Glycine, 16.0 mM Tris, pH 8.0 |
| D | 50 mM Glycine, 19.6 mM Tris, pH 8.2 |
| E | 50 mM Glycine, 28.4 mM Tris, pH 8.4 |
| F | 50 mM Glycine, 37.2 mM Tris, pH 8.6 |
| G | 50 mM Glycine, 64.0 mM Tris, pH 8.8 |
| H | 50 mM Glycine, 100 mM Tris, pH 9.0 |

TABLE 10

| NaCl levels (in mM) and Protein Challenges (mg/mL) in Each Well | | | | | | | | | | | | |
| --- | --- | --- | --- | --- | --- | --- | --- | --- | --- | --- | --- | --- |
| | All Rows | | | | | | | | | | | |
| | 1 | 2 | 3 | 4 | 5 | 6 | 7 | 8 | 9 | 10 | 11 | 12 |
| NaCl (mM) | 0 | 10 | 20 | 40 | 60 | 80 | 0 | 10 | 20 | 40 | 60 | 80 |
| MAb-AAB (mg/mL) | 5 | 5 | 5 | 5 | 5 | 5 | 132 | 132 | 132 | 132 | 132 | 132 |

In the first stage of the high-throughput screen, each well was equilibrated in the conditions of NaCl and pH as described in Tables 9 and 10 in a phase volume ratio of 6:1 (300 uL solution: 50 uL resin). The plate was shaken for 20 minutes, allowing equilibrium to be reached. The solution was then removed by centrifuging the filter plate. This equilibration cycle was repeated three times.

In the second stage, the resin in each well was challenged with a concentrated MAb-AAB solution to 5 mg/mL of resin with a volume ratio of 6:1 (300 uL solution: 50 uL resin) at the appropriate NaCl concentration and pH. A 36 mg/mL solution of Mab-AAB in 1 mM HEPES, 10 mM NaCl, pH 7.0 spiked with 300 ppm of Protein A was used as stock solution. The loaded plate was shaken for 20 minutes, allowing the resin and solution to equilibrate. The supernatant was removed from the filter plate by centrifugation and collected into a collection plate. The protein concentration in the supernatant in each well was determined by absorbance at A280 nm.

In the third stage, resin was washed by adding solutions of the specified NaCl and pH conditions listed in Table 10. The supernatant was removed after shaking for 20 minutes. In the fourth stage, 2 M NaCl was added to remove the remaining protein that was bound to the resin. The partition coefficients were calculated for each well using the mass eluted from stages 3 and 4 and the product concentration from stage 2, and are shown in Table 11.

TABLE 11

Partition Coefficients (Kp) for the 96-well HTS Screen for MAb-AAB

|   | 1 | 2 | 3 | 4 | 5 | 6 | 7 | 8 | 9 | 10 | 11 | 12 |
|---|---|---|---|---|---|---|---|---|---|----|----|----|
| A | 0.22 | 0.32 | 0.35 | 0.17 | 0.24 | 0.23 | 0.21 | 0.24 | 0.21 | 0.19 | 0.17 | 0.16 |
| B | 0.37 | 0.36 | 0.38 | 0.25 | 0.24 | 0.08 | 0.28 | 0.26 | 0.22 | 0.24 | 0.18 | 0.16 |
| C | 0.63 | 0.48 | 0.47 | 0.27 | 0.15 | 0.20 | 0.31 | 0.28 | 0.26 | 0.20 | 0.23 | 0.16 |
| D | 1.24 | 1.12 | 0.68 | 0.36 | 0.30 | 0.17 | 0.42 | 0.39 | 0.34 | 0.23 | 0.23 | 0.18 |
| E | 3.24 | 1.89 | 1.05 | 0.59 | 0.35 | 0.15 | 0.68 | 0.58 | 0.41 | 0.29 | 0.21 | 0.18 |
| F | 8.37 | 3.37 | 1.56 | 0.61 | 0.31 | 0.32 | 0.87 | 0.74 | 0.51 | 0.32 | 0.25 | 0.21 |
| G | 18.36 | 9.49 | 3.16 | 0.82 | 0.49 | 0.34 | 0.91 | 0.88 | 0.69 | 0.39 | 0.24 | 0.20 |
| H | 125.73 | 23.79 | 6.58 | 1.23 | 0.58 | 0.43 | 1.18 | 1.02 | 0.78 | 0.42 | 0.27 | 0.24 |

As shown in Table 11, the Kp value can be used to describe regions where MAb-AAB binds to the TMAE medium with different strengths. The strength of MAb-AAB binding to the TMAE medium can be manipulated by varying conditions of pH and chloride concentration into flow-through (K<0.1), weak partitioning (0.1<K<20), and binding zones (K>20).

The supernatant from the load stage of all wells from each zone were sampled and submitted for Protein A analysis. The assay results of these samples are summarized in Table 12. There is a region of pH and conductivity in which the TMAE chromatography step provides very significant removal of Protein A with limited protein loss to the resin. This region was found to be closely correlated to the partition coefficient value, Kp, and not any specific pH or chloride concentration.

Example 7.2

Column Runs Under Flow-Through Conditions

The following experiment was performed in the flow-through (FT) mode, where the MAb-AAB interacts only very weakly with the column. Two runs were performed with load challenges of 10 mg/ml and 200 mg/ml of resin.

For all TMAE (HiCapM) anion exchange chromatography runs described, the following conditions were used (exceptions are noted in the individual experimental descriptions).

Operational flow rate—150-300 cm/hr
Equilibration 1—50 mM Tris, 2.0 M NaCl, pH 7.5 (5 column volumes)
Equilibration 2—as specified, approximately equivalent to the load pH and chloride content
Post-load wash—as specified, approximately equivalent to the load pH and chloride content
Strip buffer—50 mM Tris, 2.0 M NaCl, pH 7.5 (5 column volumes)

Mabselect Protein A Chromatography

The culture containing the monoclonal antibody was purified at Pilot scale using a MabSelect column (2,389 mL) connected to a Millipore K-prime 400 chromatography system. A Mabselect Protein A column was equilibrated with 5 column volumes of 50 mM Tris/150 mM NaCl, pH 7.5 at a flow rate of 300 cm/hr. The column was then loaded at a load of approximately 40 mg product/ml resin. This was followed by a 5 column volume (CV) wash in 1 M NaCl, 50 mM Tris, pH 7.5, and a 5 CV wash containing 10 mM Tris, 75 mM NaCl, pH 7.5 wash. The column was then eluted using 50 mM glycine, 75 mM NaCl, pH 3.0. The product pool was neutralized to pH 7.6 using 2 M Tris, pH 8.5. The neutralized peak had a chloride concentration of approximately 90 mM.

TABLE 12

Protein A Log Removal Values (LRV) for MAb-AAB binding data from HTS Screen

|   | 1 | 2 | 3 | 4 | 5 | 6 | 7 | 8 | 9 | 10 | 11 | 12 |
|---|---|---|---|---|---|---|---|---|---|----|----|----|
| A | 2.11 | 1.89 | 2.12 | 1.85 | 1.22 | 1.00 | 1.63 | 1.02 | 1.00 | 0.92 | 0.85 | 1.02 |
| B | 2.79 | 2.37 | 2.42 | 1.96 | 1.23 | 1.13 | 1.77 | 1.81 | 1.22 | 0.85 | 0.94 | 1.52 |
| C | >3.05 | >3.03 | 2.74 | 2.16 | 1.37 | 1.11 | 2.25 | 2.15 | 1.96 | 1.16 | 1.06 | 0.95 |
| D | >3.41 | >2.98 | >3.06 | 2.50 | 1.94 | 1.18 | 3.39 | 3.11 | 2.57 | 1.41 | 1.02 | 0.89 |
| E | >2.87 | >2.93 | >3.01 | >2.95 | 2.13 | 1.75 | >3.09 | 3.27 | 3.09 | 1.66 | 1.89 | 0.99 |
| F | >2.64 | >2.89 | >2.99 | >3.11 | 2.29 | 1.82 | >3.07 | >3.11 | >3.15 | 2.19 | 1.24 | 0.84 |
| G | >2.33 | >2.58 | >2.89 | >3.07 | 2.41 | 2.14 | >3.09 | >3.11 | >3.14 | 2.80 | 1.46 | 0.85 |
| H | >1.63 | >2.36 | >2.76 | >3.01 | 2.86 | 2.37 | >2.98 | >3.05 | >3.15 | 3.16 | 3.45 | 0.85 |

TMAE HiCap (M) Chromatography

The neutralized Protein A pool was further purified over the TMAE step with the equilibration, load, and wash solutions at pH 7.5 with 50 mM Tris and 75 mM sodium chloride. Five column volumes of wash were used. The column dimensions and load challenges for these two studies were: Run 1: 7.0 cm diameter×20.6 cm bed height (volume—793 mL) with a load concentration of 11.9 mg/mL; and Run 2: 7.0 cm diameter×13 cm bed height (volume—500 mL) with a load concentration of 17.6 mg/mL.

These load conditions were in the flow-through (FT) region (Table 13). Batch binding studies were used to measure the partition coefficient (Kp), and the bound product was determined by protein in the column strip by using UV absorbance. This method of determining the bound product typically underestimates the amount of product bound during the load due to isocratic elution of the product during the wash. The levels of Protein A, HCP and high molecular weight aggregates (HMW) in the load and product pool were measured, and the extent of removal calculated. The results are presented in Table 13. There is poor removal of Protein A and HMW, and modest reduction in HCP levels.

TABLE 13

Removal of HCP, Protein A, and HMW under FT Conditions

| Run | Load Challenge (mg/mL) | Partition Coefficient (Kp) | Bound Product (mg/mL resin) | HCP (LRV) | Protein A (LRV) | HMW (Fold) | Recovery (%) |
|---|---|---|---|---|---|---|---|
| 1 | 110 | 0.17 | 1.4 | 2.3 | 0.1 | — | 96 |
| 2 | 200 | 0.17 | 3.3 | 2.0 | <0.1 | 1.5 | 96 |

* Impurity levels were 38.5 ppm ProA and 51,943 ppm HCP (Run 1), 8.8 ppm ProA and 25,398 ppm HCP (Run 2).

Example 7.3

Column Runs Under Weak Partitioning Conditions

High Product Challenge

TMAE (HiCap M) Anion Exchange Chromatography

Several Mabselect Protein A runs were performed essentially as described in Example 7.2 to generate the load material for these runs. The partially purified antibody pool from the Protein A step was further purified over the TMAE column. The load to the TMAE column was in 50 mM Tris, pH 8.2. The column diameter was 0.5 cm and the bed height was 10 cm bed height (volume—2.0 mL). The column was challenged to a load of 500 mg/mL resin, with a load concentration of 27.7 mg/mL.

The column was equilibrated with 5 CV of a solution containing 50 mM Tris, 2M NaCl, pH 7.5 followed by another equilibration step comprising a 50 mM Tris, pH 8.2 solution. The column was then loaded to 500 mg product/ml resin with the neutralized Protein A peak from the previous step and the product was recovered in the column effluent during the load cycle and some column volumes of the wash fraction.

These load conditions are in the weak partitioning region. Batch binding studies were used to measure the partition coefficient (Kp), and product binding at high protein concentrations. At pH 8.2, and an approximate chloride content of 12 mM, the partition coefficient, Kp, is estimated to be 1.9 (from interpolation of the dataset from the HTS screen).

The levels of HCP and Protein A were measured in three fractions during the loading stage representing load challenges of approximately 250, 375, and 500 mg/ml of resin. The results from example 7.3 are presented in Table 14. These results demonstrate that very high product challenges can be achieved in weak partitioning mode, without breakthrough of impurities. Excellent reduction in both HCP and Protein A was achieved, along with a 50% reduction in HMW content. In comparison to the results for operation in the flow-through mode in Table 13, the removal of impurities was much better in the weak partitioning mode.

TABLE 14

Removal of HCP, Protein A and HMW for a 500 mg/ml TMAE load challenge

| | Early fraction (250 mg/ml) | Middle fraction (375 mg/ml) | Late fraction (500 mg/ml) | Final product pool (ppm) |
|---|---|---|---|---|
| Residual HCP ppm (ng/mg product) | <7.6 | <7.6 | <7.6 | <7.6 |
| HCP Log Removal Value (LRV) | >3.5 | >3.5 | >3.5 | >3.5 |
| Residual Protein A ppm (ng/mg product) | 0.3 | Not determined | 0.1 | 0.6 |
| ProA Log Removal Value (LRV) | 2.9 | Not determined | 2.3 | 2.5 |
| HMW | Not determined | Not determined | Not determined | 2 fold removal |

* The impurities in the load were 25,398 ppm of HCP, 99.5 ppm of Protein A, and 2.3% HMW

Example 7.4

Column Runs Under Weak Partitioning Conditions (Robustness Studies)

To further confirm the performance of the TMAE column in the region of weak partitioning, several runs were designed varying the pH and NaCl concentration in the load to test process robustness. All runs were performed at a load challenge of 250 mg/ml resin. Several Mabselect Protein A runs were performed essentially as described in Example 7.2 to generate the load material for these runs. The only factor varied in those runs was the sodium chloride concentration in the Protein A elution, which was varied to match the NaCl concentration in the TMAE load for a particular experiment. The columns were equilibrated with Equil 2 buffers and washed with Wash buffers which had approximately the same pH and sodium chloride content of the load.

These load conditions are in the weak partitioning region. Batch binding studies were used to measure the partition coefficient (Kp). The runs are ranked by the partition coefficients listed in Table 15. The bound product was determined by measuring the protein in the column strip using UV absorbance, and ranges from 7.8-25.3 mg/mL. Protein A, HCP and HMW results from these experiments are also presented in Table 15. The removal of all impurities was found to be robust in operating ranges which cover 13.5-38.8 mM total chloride and pH 7.8-8.4.

TABLE 15

Process Robustness Studies on Removal of HCP, Protein A, and HMW in WP Mode

| NaCl Concentration (mM) | Kp | Bound Product (mg/mL) | pH | HCP in Load (ppm) | Protein A in load (ppm) | HCP (LRV) | Protein A (LRV) | HMW (Fold) | Recovery (%) |
|---|---|---|---|---|---|---|---|---|---|
| 38.8 | 0.26 | 9.4 | 7.8 | 26,391 | 493.5 | 3.7 | 1.8 | 2.0 | 92 |
| 13.5 | 0.41 | 7.9 | 7.8 | 12,821 | 69.2 | 3.3 | >1.9 | 1.8 | 87 |
| 27.4 | 0.50 | 8 | 8.0 | 23,465 | 252 | 3.6 | 2.2 | 3.2 | 91 |
| 18.5 | 0.73 | 7.8 | 8.0 | 21,626 | 308 | 3.7 | >3.2 | 2.9 | 90 |
| 23.5 | 0.80 | 9.5 | 8.1 | 18,004 | 343 | 3.2 | >3.2 | 3.5 | 94 |
| 27.7 | 0.86 | 9.5 | 8.2 | 24,821 | 280 | 3.6 | >3.2 | 2.6 | 99 |
| 18.5 | 1.48 | 10 | 8.2 | 17,669 | 252 | 3.7 | >3.1 | 3.9 | 95 |
| 22.0 | 5.35 | 25.3 | 8.4 | 29,293 | 533 | 3.6 | >2.9 | 2.3 | 90 |

\* Impurity levels were 38.5 ppm ProA and 51,943 ppm HCP (Run 1), 8.8 ppm ProA and 25,398 ppm HCP (Run 2).
+ includes the Cl− ion contribution from NaCl, buffers and titrants

Example 7.5

Summary

From these studies, it can be seen that Protein A removal (LRV) varies strongly with Kp, while HCP LRV is excellent at all the values of Kp at or above 0.26, but much reduced at Kp=0.17 (under flow-through conditions). Host cell protein removal is over one log lower for flow-through conditions compared to weak partitioning conditions, even for a reduced load challenge. The bound product ranges from 7.8-25 mg/ml for these weak partitioning conditions on this combination of resin and monoclonal antibody. The partition coefficient appears to be optimal between 0.41<Kp<5.4. It does not appear to be optimal at Kp=0.17 and a bound product of 1.4-3.3 mg/mL, the conditions of Example 7.2.

These studies suggest an alternative mode of purifying a polypeptide produced using rational design media cell culture, which will significantly reduce the presence of impurities, high molecular weight aggregates, DNA, host cell proteins, etc.

What is claimed is:

1. A method of producing a polypeptide in a cell culture comprising:
   (1) providing a cell culture, comprising:
      a. cells, comprising a nucleic acid encoding a polypeptide of interest; and
      b. a cell culture medium, comprising between 7 mM and 30 mM leucine; between 7 mM and 30 mM lysine; between 7 mM and 30 mM threonine; between 7 mM and 30 mM proline; and between 7 mM and 30 mM valine; and
   (2) maintaining the cell culture under conditions that allow expression of the polypeptide of interest.

2. The method of claim 1, further comprising a method of recovering a purified polypeptide from a load fluid, comprising the steps of:
   passing the load fluid through a medium in a column at operating conditions that cause the medium to bind at least 2.8 mg of polypeptide per mL of medium, wherein the medium is selected from the group consisting of a charged ion exchange medium, a hydrophobic interaction chromatography resin, and an immobilized metal affinity chromatography resin; and
   recovering the purified polypeptide from the column effluent.

3. The method of claim 1, further comprising a method of recovering a purified polypeptide from a load fluid, comprising the steps of:
   passing the load fluid through a medium in a column at operating conditions defined by a partition coefficient of at least 0.1; and
   recovering the purified polypeptide from the column effluent.

4. The method of claim 1, wherein the cell culture medium comprises greater than or equal to 3 mM tyrosine.

5. The method of claim 1, wherein the combined concentration of leucine, lysine, threonine, and valine in the desired cell culture medium is between about 60% and about 80% of the concentration of the total essential amino acids in the desired cell culture medium.

6. The method of claim 1, wherein the combined concentration of the essential amino acids in the desired cell culture medium is between about 30% and about 50% of the concentration of the total amino acids in the desired cell culture medium.

7. The method of claim 1, wherein the concentration of amino acids in the desired cell culture medium is between 120 mM and 350 mM.

8. The method of claim 1, wherein the cell culture is a large-scale cell culture.

9. The method of claim 1, wherein the cells are animal cells.

10. The method of claim 1, wherein the polypeptide is purified.

11. The method of claim 1, wherein the medium is a defined medium.

12. A method of producing a polypeptide in a cell culture comprising:
(1) providing a cell culture, comprising:
   a. cells, comprising a nucleic acid encoding a polypeptide of interest; and
   b. a cell culture medium, wherein the combined concentration of leucine, lysine, threonine, proline, and valine in the cell culture medium is between 35 mM and 150 mM, and wherein the concentration of amino acids in the cell culture medium is between 120 mM and 350 mM; and
(2) maintaining the cell culture under conditions that allow expression of the polypeptide of interest.

13. The method of claim 12, wherein the concentration of proline in the cell culture is maintained at greater than 1 mM.

14. The method of claim 12, wherein the concentration of proline in the cell culture is maintained at greater than 2 mM.

15. A method of producing a polypeptide in a cell culture comprising:
(1) providing a cell culture, comprising
   a. cells, comprising a nucleic acid encoding a polypeptide of interest; and
   b. a starting cell culture medium, wherein the volume of the starting cell culture medium is about 60-99% of the volume of a desired cell culture medium volume;
(2) providing a feeding cell culture medium to the cell culture according to step (1), wherein the volume of the feeding cell culture medium is about 1-40% of the desired cell culture medium volume, and wherein the resulting desired cell culture medium comprises between 7 mM and 30 mM leucine; between 7 mM and 30 mM lysine; between 7 mM and 30 mM threonine; between 7 mM and 30 mM proline; and between 7 mM and 30 mM valine; and
(3) maintaining the cell culture under conditions that allow expression of the polypeptide of interest.

* * * * *